(12) United States Patent
Amit et al.

(10) Patent No.: US 8,329,870 B2
(45) Date of Patent: Dec. 11, 2012

(54) WATER SOLUBLE REACTIVE DERIVATIVES OF CARBOXY POLYSACCHARIDES AND FIBRINOGEN CONJUGATES THEREOF

(75) Inventors: Boaz Amit, Kiryat Ono (IL); Hilla Barkay-Olami, Rishon Le Zion (IL); Avner Yayon, Moshav Sitria (IL)

(73) Assignee: Hepacore Ltd., Ness Ziona (IL)

( * ) Notice: Subject to any disclaimer, the term of this patent is extended or adjusted under 35 U.S.C. 154(b) by 518 days.

(21) Appl. No.: 12/522,092

(22) PCT Filed: Jan. 6, 2008

(86) PCT No.: PCT/IL2008/000033
§ 371 (c)(1),
(2), (4) Date: Nov. 11, 2009

(87) PCT Pub. No.: WO2008/081463
PCT Pub. Date: Jul. 10, 2008

(65) Prior Publication Data
US 2010/0086594 A1 Apr. 8, 2010

Related U.S. Application Data

(60) Provisional application No. 60/878,391, filed on Jan. 4, 2007.

(51) Int. Cl.
*A61K 9/14* (2006.01)
*A61K 38/00* (2006.01)
*A61K 35/14* (2006.01)
*A01N 43/04* (2006.01)
*C07K 1/00* (2006.01)
*C07K 14/00* (2006.01)
*C07K 16/00* (2006.01)
*C07K 17/00* (2006.01)

(52) U.S. Cl. .......... 530/382; 514/1.1; 514/54; 424/484
(58) Field of Classification Search .................. None
See application file for complete search history.

(56) References Cited

U.S. PATENT DOCUMENTS

| | | | |
|---|---|---|---|
| 2,492,458 A * | 12/1949 | Bering, Jr. | 424/443 |
| 4,582,865 A | 4/1986 | Balazs et al. | 524/29 |
| 4,642,120 A | 2/1987 | Nevo et al. | 623/16 |
| 4,713,448 A | 12/1987 | Balazs et al. | 536/55.1 |
| 5,128,326 A | 7/1992 | Balazs et al. | 514/54 |
| 5,209,776 A | 5/1993 | Bass et al. | 106/124 |
| 5,260,420 A | 11/1993 | Burnouf-Radosevich et al. | 530/382 |
| 5,290,918 A | 3/1994 | Bui-Khac | 530/381 |
| 5,411,885 A | 5/1995 | Marx | 435/240.2 |
| 5,616,568 A | 4/1997 | Pouyani et al. | 514/54 |
| 5,631,011 A | 5/1997 | Wadström | 424/400 |
| 5,760,200 A | 6/1998 | Miller et al. | 536/21 |
| 5,763,410 A | 6/1998 | Edwardson et al. | 514/21 |
| 5,856,299 A | 1/1999 | Righetto et al. | 514/8 |
| 5,874,417 A | 2/1999 | Prestwich et al. | 514/54 |
| 5,972,385 A | 10/1999 | Liu et al. | 424/486 |
| 6,030,958 A | 2/2000 | Burns et al. | 514/57 |
| 6,074,663 A | 6/2000 | Delmotte et al. | 424/443 |
| 6,174,999 B1 | 1/2001 | Miller et al. | 536/21 |
| 6,274,090 B1 | 8/2001 | Coelho et al. | 422/101 |
| 6,310,267 B1 | 10/2001 | Rapp | 602/41 |
| 6,334,968 B1 | 1/2002 | Shapiro et al. | 264/28 |
| 6,398,816 B1 | 6/2002 | Breitbart et al. | 623/23.72 |
| 6,425,918 B1 | 7/2002 | Shapiro et al. | 623/11.11 |
| 6,440,427 B1 | 8/2002 | Wadström | 424/400 |
| 6,482,231 B1 * | 11/2002 | Abatangelo et al. | 623/11.11 |
| 6,486,377 B2 | 11/2002 | Rapp | 602/41 |
| 6,503,527 B1 | 1/2003 | Whitmore et al. | 424/422 |
| 6,630,457 B1 | 10/2003 | Aeschlimann et al. | 514/54 |
| 6,699,484 B2 | 3/2004 | Whitmore et al. | 424/400 |
| 6,943,154 B2 | 9/2005 | Miller et al. | 514/53 |
| 7,009,039 B2 | 3/2006 | Yayon et al. | 530/381 |
| 2004/0120993 A1 * | 6/2004 | Zhang et al. | 424/445 |
| 2005/0142163 A1 * | 6/2005 | Hunter et al. | 424/423 |
| 2006/0159733 A1 | 7/2006 | Pendharkar et al. | 424/445 |
| 2011/0091443 A1 * | 4/2011 | Kim et al. | 424/94.64 |

FOREIGN PATENT DOCUMENTS

| | | |
|---|---|---|
| EP | 0111311 B1 | 6/1984 |
| EP | 0325270 A2 | 7/1989 |
| JP | 60101101 A * | 6/1985 |
| WO | WO 92/20349 A1 | 11/1992 |
| WO | WO 95/24429 A1 | 9/1995 |
| WO | WO 99/15209 A1 | 4/1999 |
| WO | WO 00/01733 A1 | 1/2000 |
| WO | WO 00/16818 A1 | 3/2000 |
| WO | WO 00/51538 A1 | 9/2000 |
| WO | WO 02/100440 A1 | 12/2002 |
| WO | WO 03/007873 A2 | 1/2003 |
| WO | WO 03/087160 A1 | 10/2003 |
| WO | WO 03/094835 A2 | 11/2003 |

(Continued)

OTHER PUBLICATIONS

Matsuzaki et al. JP60101101 A, Jun. 1985. abstract in English, 1 page.*
Almany L. et al., "Biosymthetic hydrogel scaffolds made from fibrinogen and polyethylene glycol for 3D cell cultures" Biomaterials, Elsevier Science Publishers BV., Barking, GB, vol. 26, No. 15, May 1, 2005, pp. 2467-2477.
Bulpitt P and Aeschlimann D. 1999. New strategy for chemical modification of hyaluronic acid: Preparation of functionalized derivatives and their use in the formation of novel biocompatible hydrogels. J. Biomed. Mater. Res. 47:2, 152-169.
Gilles MA, Hudson AQ and Borders CL Jr. 1990. Stability of Water-Soluble Carbodiimides in Aqueous Solution. Anal. Biochem. 184, 244-248.

(Continued)

*Primary Examiner* — Marcela M Cordero Garcia
(74) *Attorney, Agent, or Firm* — Winston & Strawn LLP

(57) ABSTRACT

The present invention provides water-soluble reactive esters of carboxy polysaccharides and derivatives thereof. The reactive carboxy polysaccharide derivatives are useful per se in aqueous solutions or specifically for the formation of water-soluble covalent fibrinogen conjugates. A preferred conjugate is a hyaluronic acid-fibrinogen conjugate and fibrin adhesive, clot or matrix derived from it. Methods of preparation and methods of use in tissue repair and regeneration are also disclosed.

29 Claims, 5 Drawing Sheets

FOREIGN PATENT DOCUMENTS

| WO | WO 2004/067704 A2 | 8/2004 |
| WO | WO 2007/026362 A2 | 3/2007 |
| WO | WO 2007/102149 A2 | 9/2007 |

OTHER PUBLICATIONS

Haisch A, Loch A, David J, Prub A, Hansen R and Sittinger M. 2000. Preparation of a pure autologous biodegradable fibrin matrix for tissue engineering. Med. Biol. Eng. Comput. (Cell Eng.) 38:6, 686-89.

Itokazu M, Yamamoto K, Yang WY, Aoki T, Kato N and Watanabe K. 1997. The Sustained Release of Antibiotic from Freeze-Dried Fibrin-Antibiotic Compound and Efficacies in a Rat Model of Osteomyelitis. Infection. 25:6, 359-363.

LeBoeuf RD, Raja RH, Fuller GM and Weigel PH. 1986. Human Fibrinogen Specifically Binds Hyaluronic Acid. J. Biol. Chem. 261:27, 12586-12592.

LeBoeuf RD, Gregg RR, Weigel PH and Fuller GM. 1987. Effects of Hyaluronic Acid and Other Glycosaminoglycans on Fibrin Polymer Formation. Biochem. 26:19, 6052-6057.

Li H, Liu Y, Shu XZ, Gray SD and Prestwich GD. 2004. Synthesis and Biological Evaluation of a Cross-Linked Hyaluronan-Mitomycin C Hydrogel. Biomacromol. 5:3, 895-902.

Luo Y and Prestwich GD. 2001. Hyaluronic Acid-N-hydroxysuccinimide: A Useful Intermediate for Bioconjugation. Bioconj. Chem. 12, 1085-1088.

McKee PA, Mattock P and Hill RL. 1970. Subunit Structure of Human Fibrinogen, Soluble Fibrin, and Cross-Linked Insoluble Fibrin. Proc. Nat. Acad. Sci. 66, 738-744.

Pouyani T and Prestwich GD. 1994. Functionalized Derivatives of Hyaluronic Acid Oligosaccharides: Drug Carriers and Novel Biomaterials. Bioconj. Chem. 5, 339-347.

Prestwich GD, Marecak DM, Marecek JF, Vercruysse KP and Ziebel MR. 1998. Controlled chemical modification of hyaluronic acid: Synthesis, applications, and biodegradation of hydrazide derivatives. J. Cont. Release. 53, 93-103.

Sakurai K, Miyazaki K, Kodera Y, Nishimura H, Shingu M and Inada Y. 1997. Anti-inflammatory activity of superoxide dismutase conjugated with sodium hyaluronate. Glycoconj. J. 14, 723-728.

Shu XZ, Ghosh K, Liu Y, Palumbo FS, Luo Y, Clark RA and Prestwich GD. 2004 Attachment and spreading of fibroblasts on an RGD peptide-modified injectable hyaluronan hydrogel. J. Biomed. Mat. Res. 68A:2, 365-375.

Trudel S, Stewart AK, Rom E, Wei E, Li ZH, Kotzer S, Chumakov I, Singer Y, Chang H, Liang SB and Yayon A. 2006. The inhibitory anti-FGFR3 antibody, PRO-001, is cytotoxic to (4;14) multiple myeloma cells. Blood. 107:10, 4039-4046.

International Search Report of International Application No. PCT/IL2008/000033 Mailed Nov. 6, 2008.

* cited by examiner

WATER SOLUBLE REACTIVE DERIVATIVES OF CARBOXY POLYSACCHARIDES AND FIBRINOGEN CONJUGATES THEREOF

This application is a 371 filing of International Patent Application PCT/IL2008/000033 filed on Jan. 6, 2008, which claims the benefit of application No. 60/878,391 filed Jan. 4, 2007.

FIELD OF THE INVENTION

The present invention relates to water-soluble reactive ester derivatives of carboxy polysaccharides. The present invention further relates to conjugates of said carboxy polysaccharides with fibrin(ogen), compositions comprising the carboxy polysaccharide conjugates, processes for their preparation, and to their use in tissue repair and regeneration.

BACKGROUND OF THE INVENTION

Natural and synthetic carboxy polysaccharides as well as their reactive derivatives are utilized in a variety of clinical applications, including the preparation of medical devices. The term "reactive carboxy polysaccharide derivatives" refers to a polysaccharide in which a part or all of the carboxy moieties have been modified into active functional groups, e.g., active esters having higher reactivity with nucleophiles than the corresponding carboxylic acid functionality. The hitherto known active esters of polysaccharides are highly insoluble in water. Their reactivity with hydrophilic nucleophiles including proteins and the like is restricted by the need of aprotic solvents.

U.S. Pat. No. 5,856,299 discloses isolated reactive esters of carboxy polysaccharides prepared in an aprotic solvent. These active esters were suggested for preparing activated polysaccharide-based surfaces which can further bind polypeptides or proteins by a nucleophilic substitution reaction. However, the subsequent conjugation of these isolated active esters with nucleophiles requires the use of an aprotic solvent as well, thus limiting the conjugation reactions to proteins or polypeptides miscible in aprotic solvents. Moreover, in order to obtain an isolated esterified polysaccharide, precipitation is required.

Hyaluronic Acid

Hyaluronic acid (hyaluronate, HA), a glycosaminoglycan, is a ubiquitous component of the extracellular matrix (ECM) of all connective tissues. HA is a linear polysaccharide composed of a disaccharide-repeating unit of N-acetyl-D-glucosamine and D-glucuronic acid linked by $\beta$1-4 and $\beta$1-3 linkages. HA has a range of naturally occurring molecular weights from several thousands to over 10 million Daltons.

The unique viscoelastic properties of HA combined with its biocompatibility and immunoneutrality has led to its use in a variety of clinical applications such as eye surgery and visco-supplementation of joints. HA is known to specifically bind proteins in the ECM and on the cell surface. These interactions are important for stabilizing the cartilage matrix, in cell motility, in cellular proliferation, in wound healing and inflammation as well as in cancer metastasis. Hyaluronic acid was shown to reversibly bind fibrinogen, and this binding alters the formation kinetics of fibrin gels (LeBoeuf et al., 1986; LeBoeuf et al., 1987).

A variety of chemical modifications and crosslinking strategies of native HA have been explored in order to obtain more mechanically robust and more metabolically stable HA derivatives. The principle targets for chemical modification of HA are the hydroxyl and carboxyl moieties. Modifications via the hydroxyl functional groups are primarily useful for the preparation of crosslinked HA by reactions with bifunctional cross linkers, e.g. divinyl sulfone and diglycidyl ethers (U.S. Pat. Nos. 4,582,865 and 4,713,448).

Modifications of the carboxylic functional groups are useful for the introduction of pendant functionalities, which can further be used to obtain crosslinked products or as sites for covalent attachment of various chemicals, e.g. drugs and biochemical reagents (Li et al., 2004; Shu et al., 2004; Bulpitt and Aeschlimann, 1999). These modifications are made using hydrazides or amines. Activation of HA carboxylic functional groups towards nucleophilic attack by hydrazides or amines in an aqueous media, is mainly performed by the use of water-soluble carbodiimides, particularly 1-ethyl-3-[3-dimethylaminopropyl]carbodiimide (EDC). Two major procedures for performing said activation are known in the art. The first, developed by Prestwich et al. is disclosed in U.S. Pat. Nos. 5,616,568 and 5,874,417, Prestwich et al. 1998, and Pouyani and Prestwich, 1994. A second procedure is disclosed in U.S. Pat. No. 6,630,457 wherein HA derivatives with pendant hydrazido, amino as well as other functional groups, are formed. WO 07/102,149 to some of the inventors of the present invention discloses hydrazido derivatives of HA. The disclosures of the aforementioned patents are incorporated by reference in their entirety herein.

WO 00/01733 discloses amide derivatives of hyaluronic acid and methods of preparation thereof. The application further teaches biomaterials prepared from the amide derivatives which can be associated with various polymers, including proteins and polysaccharides. There is neither teaching nor suggestion of a HA-fibrin(ogen) conjugate.

U.S. Pat. No. 5,128,326 discloses drug delivery gels based on cross-linked hyaluronic acid or alternatively, hyaluronic acid and a hydrophilic polymer either polysaccharide, protein or glycoprotein. The drug may be dispersed within the gel or may be covalently attached to either of the HA or hydrophilic polymer. A recently published international application WO 07/026,362 discloses a method of preparing cross-linked polysaccharide matrices by cross-linking amino functionalized polysaccharides including amino functionalized HA with reducing sugars and/or sugar derivatives. The resulting matrices include polysaccharides cross-linked with proteins and/or polypeptides. There is neither teaching nor suggestion of a soluble HA-fibrin(ogen) conjugate.

U.S. Pat. Nos. 5,760,200, 6,030,958, 6,174,999 and 6,943,154 disclose water insoluble HA-based biocompatible compositions, formed in an aqueous medium. These compositions were prepared by combining: (a) a polyanionic polysaccharide (b) at least 1 molar equivalent of a nucleophile per molar equivalent of the polyanionic polysaccharide, and (c) at least 0.1 molar equivalent of an activating agent per molar equivalent of said polyanionic polysaccharide, in a "one pot reaction".

Hyaluronic acid is easily and readily crosslinked, thereby allowing the formation of heterogeneous hyaluronic acid compounds. U.S. Pat. No. 5,972,385 discloses a lyophilized crosslinked collagen-polysaccharide matrix for tissue repair in which collagen is covalently bound to periodate-treated polysaccharide having free aldehyde groups. The crosslinked collagen-polysaccharide forms a slurry, which is poured into a mold and lyophilized to form a sponge. A collagen-polysaccharide matrix further comprising fibrin is disclosed as well.

U.S. Pat. Nos. 6,503,527 and 6,699,484 disclose a fibrin sealant or fibrin adhesive composition comprising fibrinogen, a fibrinogen-cleaving agent and a biomaterial which is a hyaluronic acid material, a chitin material or a chitosan material wherein both the fibrinogen and the fibrinogen-cleaving agent are incorporated on the biomaterial. According to these disclosures, the HA or HA derivatives can be produced according to methods known in the art for derivatizing HA; active esters of HA are neither taught nor suggested. Moreover, no methods whatsoever are disclosed for forming any chemical conjugates between HA and fibrinogen. Thus, the above disclosures neither teach nor suggest a water-soluble polysaccharide-fibrinogen conjugate having a plurality of amide bonds between the carboxylic functional groups of the polysaccharide and the amino functional groups of the fibrinogen.

A water-soluble conjugate of sodium hyaluronate with superoxide dismutase (SOD) was reported by Sakurai et al. (1997). This conjugate showed improved anti-inflammatory activity in vivo. Its water solubility might be attributed to the low molecular weight of bovine SOD, which infers on the physicochemical properties of the conjugate.

Fibrin

Fibrinogen is a major plasma protein, which participates in the blood coagulation process. Upon blood vessel injury, fibrinogen is converted into insoluble fibrin, which serves as the scaffold for a clot. Blood coagulation is a complex process comprising the sequential interaction of a number of plasma proteins, in particular of fibrinogen (factor I), prothrombin (factor II), factor V and factors VII-XIII. Other plasma proteins such as Von Willebrand factor, immunoglobulins, coagulation factors and complement components also participate in the formation of blood clots.

Many fibrin(ogen) containing sealants, clots or scaffolds are known in the art. Fibrin is often used as a tissue adhesive medical device for wound healing and tissue repair. Lyophilized plasma-derived protein concentrate (comprising fibrinogen, Factor XIII and fibronectin), in the presence of thrombin and calcium ions forms an injectable biological sealant (fibrin glue). U.S. Pat. No. 5,411,885 discloses a method for embedding and culturing tissue employing fibrin glue.

U.S. Pat. No. 4,642,120 discloses the use of fibrinogen-containing glue in combination with autologous mesenchymal or chondrocytic cells to promote repair of cartilage and bone defects. U.S. Pat. No. 5,260,420 discloses a method for preparation and use of biological glue comprising plasma proteins for therapeutic use. U.S. Pat. No. 6,440,427 teaches an adhesive composition mainly composed of fibrin forming components and a viscosity enhancing polysaccharide such as hyaluronic acid.

U.S. Pat. No. 5,631,011 teaches a tissue treatment composition to promote wound healing and reduce scar formation consisting essentially of (a) a fibrin glue component comprising fibrin or fibrinogen, Factor XIII, thrombin, bivalent calcium, and (b) a hyaluronic acid component selected from hyaluronic acid, crosslinked hyaluronic acid, or a salt thereof. According to this disclosure, the hyaluronic acid component is present in an amount sufficient to form a viscous composition.

U.S. Pat. No. 5,763,410 discloses the use of kits for the preparation of a fibrin sealant containing fibrin monomer which can be polymerized to form a fibrin sealant when combined with a second component which is distilled water or an alkaline buffer.

U.S. Pat. No. 6,074,663 discloses a cross-linked fibrin sheet-like material for the prevention of adhesion formation. PCT application WO 00/51538 discloses a bioadhesive, porous PEG-crosslinked albumin and fibrin scaffold, useful for wound healing. A freeze-dried fibrin antibiotic clot for the slow release of an antibiotic is described by Itokazu et al. (1997).

A freeze-dried fibrin web for wound healing has been disclosed in U.S. Pat. Nos. 6,310,267 and 6,486,377. A fibrin sponge containing a blood clotting activator for hemostasis, tissue adhesion, wound healing and cell culture support is disclosed in WO 99/15209. WO 04/067704 of one of the applicants of the present invention discloses a porous freeze-dried fibrin matrix which incorporates glycosaminoglycans and bioactive agents for use as an implant for tissue engineering.

There is neither teaching nor suggestion of a polysaccharide-fibrinogen covalent conjugate in any of the above references.

Tissue Engineering

Tissue engineering is defined as the art of reconstructing or regenerating mammalian tissues, both structurally and functionally. It generally includes the delivery of a synthetic or natural scaffold that serves as an architectural support onto which cells may attach, proliferate, and synthesize new tissue to repair a wound or defect.

An example of a tissue that is prone to damage by disease and trauma is the articular cartilage, one of several types of cartilage in the body, found at the articular surfaces of bones. Damaged cartilage is amenable to repair.

Matrices useful for tissue regeneration and/or as biocompatible surfaces for tissue culture are well known in the art. These matrices may be considered as substrates for cell growth either in vitro or in vivo. Suitable matrices for tissue growth and/or regeneration include both biocompatible and biostable entities. Among the many candidates that may serve as useful matrices claimed to support tissue growth or regeneration are gels, foams, sheets, and porous structures of different forms and shapes.

Many natural polymers have been disclosed as useful for tissue engineering or culture, including various glycoproteins and glycosaminoglycans (GAGs) of the extracellular matrix, for instance fibronectin, various types of collagen and laminin, keratin, fibrin and fibrinogen, hyaluronic acid, heparan sulfate, chondroitin sulfate and others. U.S. Pat. Nos. 6,425,918 and 6,334,968 disclose a freeze-dried bioresorbable polysaccharide sponge and its use thereof as a matrix or scaffold for implantation into a patient.

There remains an unmet need for water-soluble carboxy polysaccharide derivatives useful per se and in the preparation of soluble polysaccharide-fibrinogen conjugates having utility in tissue engineering, repair and regeneration.

SUMMARY OF THE INVENTION

The present invention provides water-soluble reactive esters of carboxy polysaccharides. Specifically, said reactive esters are useful per se in aqueous solutions or in the preparation of water-soluble polysaccharide-fibrinogen conjugates. The invention further provides polysaccharide-fibrin clots or porous fibrin matrices derived from the water-soluble polysaccharide-fibrinogen conjugates upon mixture with a fibrinogen-cleaving agent, for example thrombin. The compositions of the present invention are useful in a variety of clinical applications, in particular for the repair and regeneration of diseased or damaged tissue. Cosmetic uses such as wrinkle smoothing applications, tissue augmentation and tissue bulking are disclosed as well.

The present invention provides, for the first time, methods for preparing water-soluble carboxy polysaccharide active esters. These novel active esters are substantially free of an activator and thus do not precipitate upon reacting with nucleophiles following the formation of multiple side products. The invention further provides a method for chemically conjugating said carboxy polysaccharide active esters to fibrinogen thus producing water-soluble polysaccharide-fibrinogen conjugates in a two-step procedure that prevents production of undesired side products. The water-soluble conjugates of the present invention are produced in high yields and can be found useful in a plurality of clinical applications.

According to some embodiments, a water-soluble hyaluronic acid-fibrinogen conjugate, which exhibits excellent clottability and is useful in a variety of applications including hemostasis and adhesion, for example as fibrin adhesive, and for tissue repair and tissue engineering, including as a scaffold for implantation is disclosed.

According to one aspect, the present invention provides an aqueous solution of a carboxy polysaccharide active ester, which is substantially free of an activator. In a preferred embodiment, the invention provides an aqueous solution of N-hydroxysuccinimide active ester substantially free of an activator. In another aspect, the present invention provides a water-soluble polysaccharide-fibrinogen conjugate wherein the conjugate comprises an amide bond between a carboxylic functional group of the polysaccharide and an amino functional group of the fibrinogen. Preferably, the conjugate comprises a plurality of amide bonds between carboxylic functional groups of the polysaccharide and amino functional groups of the fibrinogen. The present invention excludes a polysaccharide-fibrinogen conjugate in which both fibrinogen and a fibrinogen-cleaving agent are applied to or covalently bound to the polysaccharide.

In some embodiments, the carboxy polysaccharide is selected from the group consisting of a natural polysaccharide, a synthetic polysaccharide, a semi-synthetic polysaccharide, and combinations thereof.

Natural polysaccharides include, but are not limited to, glycosaminoglycans, alginate, fucoidan, galactans, galactomannans, glucomannans, xanthan gum and gellan. Glycosaminoglycans include, but are not limited to, hyaluronic acid, heparin, chondroitin sulfate, dermatan sulfate, heparan sulfate, keratan sulfate, and combinations thereof. Derivatives and salts of the above, including low molecular weight forms of the glycosaminoglycans are intended to be included in the invention.

Semi-synthetic carboxy polysaccharides include, but are not limited to, carboxyalkyl derivatives of cellulose, starch and chitin, for example, carboxyalkylcellulose. According to one embodiment, the present invention provides active esters of carboxymethylcellulose in an aqueous solution. The solution is preferably in a physiologically acceptable carrier, suitable for use in vivo per se. According to another embodiment, the active esters of carboxymethylcellulose are used for the preparation of fibrin(ogen) conjugates, clots and matrices.

In currently preferred embodiments, the carboxylated polysaccharide is hyaluronic acid (HA) and its derivatives including, but not limited to, the partial esters of hyaluronic acid with aliphatic, aryliphatic, heterocyclic and cycloaliphatic alcohols. Suitable molecular weights of hyaluronic acid and its partial esters range from about $10^4$ Daltons to about three million ($3 \times 10^6$) Daltons. The present invention therefore provides HA reactive esters in a physiological aqueous solution. In other embodiments, the carboxylated polysaccharide is heparin and its partial esters with aliphatic, aryliphatic, heterocyclic and cycloaliphatic alcohols. Hence, heparin reactive esters are within the scope of the present invention.

In one embodiment, the present invention provides a water-soluble hyaluronic acid-fibrinogen conjugate wherein the conjugate comprises an amide bond between a carboxylic functional group of the hyaluronic acid and an amino functional group of the fibrinogen.

Fibrinogen is selected from mammalian and non-mammalian fibrinogen. In some embodiments, fibrinogen is for example, human, bovine, equine, ovine or porcine fibrinogen. In certain embodiments, fibrinogen is human fibrinogen. The fibrinogen may be natural fibrinogen isolated, for example, from donor plasma; or recombinant fibrinogen.

In one embodiment, the composition comprising a water-soluble carboxy polysaccharide-fibrinogen conjugate provides the starting material for the preparation of a fibrin adhesive or a water insoluble fibrin clot. The water-soluble carboxy polysaccharide-fibrinogen conjugate can be mixed with a fibrinogen-cleaving agent, for example thrombin, to produce a water insoluble fibrin clot. The water insoluble fibrin clot can be subsequently freeze-dried to form a porous fibrin matrix or scaffold. The fibrin clot as well as fibrin matrix are within the scope of the present invention.

In another aspect, the present invention provides a carboxy polysaccharide-fibrin clot comprising water-soluble carboxy polysaccharide-fibrinogen conjugate and thrombin, wherein said conjugate comprises an amide bond between a carboxylic functional group of the polysaccharide and an amino functional group of the fibrinogen. In yet another aspect, the invention further provides a porous fibrin matrix comprising a carboxy polysaccharide-fibrin clot wherein the clot comprises an amide bond between a carboxylic functional group of the polysaccharide and an amino functional group of the fibrin.

According to another aspect, the present invention provides a composition comprising the polysaccharide-fibrinogen conjugate. Accordingly, in one aspect the present invention provides a pharmaceutical composition comprising an aqueous solution of carboxy polysaccharide active ester which is substantially free of the activator, and a pharmaceutically acceptable excipient. In a preferred embodiment, the invention provides a pharmaceutical composition comprising an aqueous solution of N-hydroxysuccinimide active ester, which is substantially free of an activator, and a pharmaceutically acceptable excipient.

In another aspect, the invention provides a water-soluble carboxy polysaccharide-fibrinogen conjugate wherein the conjugate comprises an amide bond between a carboxylic functional group of the polysaccharide and an amino functional group of the fibrinogen; and a pharmaceutically acceptable carrier or excipient. In some embodiments, the pharmaceutically acceptable carrier is water or a buffer in which the conjugate is isolated or purified.

In some embodiments, the compositions further comprise at least one bioactive agent. Exemplary suitable bioactive agents include therapeutic proteins, platelets and platelet supernatant, analgesics, anti-microbial agents, anti-inflammatory agents and enzymes. In other embodiments, the bioactive agent is a growth factor. In a preferred embodiment, the growth factor is a fibroblast growth factor (FGF) or a variant thereof.

According to one embodiment, the pharmaceutical composition is a highly stable fibrin clot. A stable fibrin clot can be produced ex vivo or in situ and is useful in the repair or regeneration of diseased or damaged tissue. The stable fibrin clot can be implanted per se or further comprising cells and or a bioactive agent. The fibrin matrix of the invention may also be used per se for clinical and biotechnological applications, or as a support for growth and differentiation of cells, both in vitro and in vivo. In a preferred embodiment, the invention provides use of the porous fibrin matrix for supporting cell growth after implantation.

The pharmaceutical composition comprising polysaccharide-fibrin clot is suitable for the treatment, repair or regeneration of injured, diseased or traumatized mammalian tissue, the use comprising the step of applying the composition of the present invention to the site of injured, diseased or traumatized tissue. The injured, diseased or traumatized tissue may be, but is not limited to, mesenchymal, endothelial, epithelial derived tissue, for example dermal, cardiac, cartilage, bone, urothelial, endocrine, neuronal, pancreatic, renal, hepatic and ocular tissue types. A currently preferred mammalian tissue is cartilage.

The composition further has use in cosmetic applications for example in the treatment of wrinkles or scars. The pharmaceutical composition may be formulated for topical or subcutaneous application.

According to another aspect, the present invention provides a method for the repair or regeneration of injured, diseased or traumatized mammalian tissue the method comprising the step of applying a pharmaceutical composition comprising carboxy polysaccharide-fibrinogen of the present invention and a fibrinogen cleaving agent to the site of injured, diseased or traumatized tissue. In some embodiments, the pharmaceutical composition is selected from a fibrin clot and a fibrin matrix.

In another aspect, the present invention provides a method for the preparation of a water-soluble reactive carboxy polysaccharide in an aqueous solution, wherein at least part of the carboxy groups are modified into active ester functional groups, the method comprising the steps of:

a) providing an aqueous solution comprising at least one carboxy polysaccharide, preferably, the aqueous solution is pH controlled using a buffer;

b) modifying at least part of the carboxy functional groups of the carboxy polysaccharide to active ester functional groups in the presence of at least one water-soluble activator and at least one alcohol; and c) removing residual activator from the solution of the water-soluble reactive polysaccharide.

In some embodiments removal of the residual carbodiimide is achieved by adding to reaction step b) a water insoluble resin having affinity to said activator. The water insoluble resin can carry a functional group that reacts chemically or interacts via ion bonding with the activator. The functional group is selected from a carboxy, phosphate and sulfate group. A preferred functional group is carboxy.

Suitable alcohols include, but are not limited to, aromatic alcohol, substituted aromatic alcohol, aromatic heterocyclic alcohol, substituted aromatic heterocyclic alcohol, N-hydroxylamine, or a combination thereof. In some embodiments, the alcohol is N-hydroxylamine selected from the group consisting of N-hydroxysuccinimide and sulfo-N-hydroxysuccinimide.

The water-soluble activator is, according to certain embodiments, water-soluble carbodiimide selected from the group consisting of (1-[3-(dimethylamino)propyl]-3-ethylcarbodiimide hydrochloride (EDC); (1-[3-(dimethylamino)propyl]-3-ethylcarbodiimide methiodide; and 1-cyclohexyl-3-(2-morpholinoethyl)carbodiimide metho-p-toluenesulfonate.

The water-soluble active esters of carboxy polysaccharide can be used per se. Alternatively, the water-soluble active esters of carboxy polysaccharide can be used in the preparation of a water-soluble carboxy polysaccharide-fibrinogen conjugate. Suitable routes of administration include, but are not limited to, topical, intralesional, intra-articular and subcutaneous applications.

The carboxy polysaccharides useful in the preparation of water-soluble active esters of carboxy polysaccharides are selected from a natural polysaccharide, a synthetic polysaccharide, a semi-synthetic polysaccharide, and combinations thereof.

According to certain embodiments, the present invention provides an aqueous solution in a physiologically acceptable carrier, comprising water-soluble active esters of carboxy polysaccharide wherein said carboxy polysaccharide active ester is formed by modifying part or all of the carboxy functional groups of the carboxy polysaccharide to active ester functional groups in the presence at least one water-soluble activator and an alcohol, and subsequently removing said activator from the aqueous solution.

In some embodiments the natural polysaccharide is a glycosaminoglycan selected from the group consisting of hyaluronic acid, heparin, heparan sulfate, chondroitin sulfate, dermatan sulfate, keratan sulfate, combinations thereof and derivatives and salts thereof. In certain preferred embodiments, the glycosaminoglycan is hyaluronic acid or its derivative including but not limited to, the partial esters of hyaluronic acid with aliphatic, aryliphatic, heterocyclic and cycloaliphatic alcohols, or salt thereof including but not limited to sodium salts, quaternary ammonium salts and the like. In other preferred embodiments, the glycosaminoglycan is heparin thus providing an aqueous solution comprising an activated ester of heparin.

In another embodiment, the present invention provides a method for the preparation of a carboxy polysaccharide-fibrinogen conjugate wherein the conjugate comprises an amide bond between a carboxylic functional group of the polysaccharide and an amino functional group of the fibrinogen. The method comprising the step of reacting an aqueous solution of water-soluble active esters of carboxy polysaccharide of the present invention with an aqueous solution comprising fibrinogen under conditions to form a water-soluble carboxy polysaccharide-fibrinogen conjugate. In preferred embodiments, the aqueous solutions are pH controlled using a buffer at a pH range of 5.5-9.

In another embodiment, the method further includes a step of purifying said water-soluble carboxy polysaccharide-fibrinogen conjugate.

In another aspect, the present invention provides a method for treating diseased or injured tissue comprising the step of administering to the site of diseased or injured tissue a therapeutic amount of a water-soluble reactive carboxy polysaccharide. In some embodiments, the tissue is cartilage, preferably articular cartilage. A method of augmenting tissue in a subject comprising the step of applying a pharmaceutical composition comprising an aqueous solution of reactive carboxy polysaccharide to the site of a dermal defect crease, is within the scope of the present invention as well.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The present invention will be understood and appreciated more fully from the following detailed description taken in conjunction with the figures in which.

DETAILED DESCRIPTION OF THE INVENTION

Figure 1:
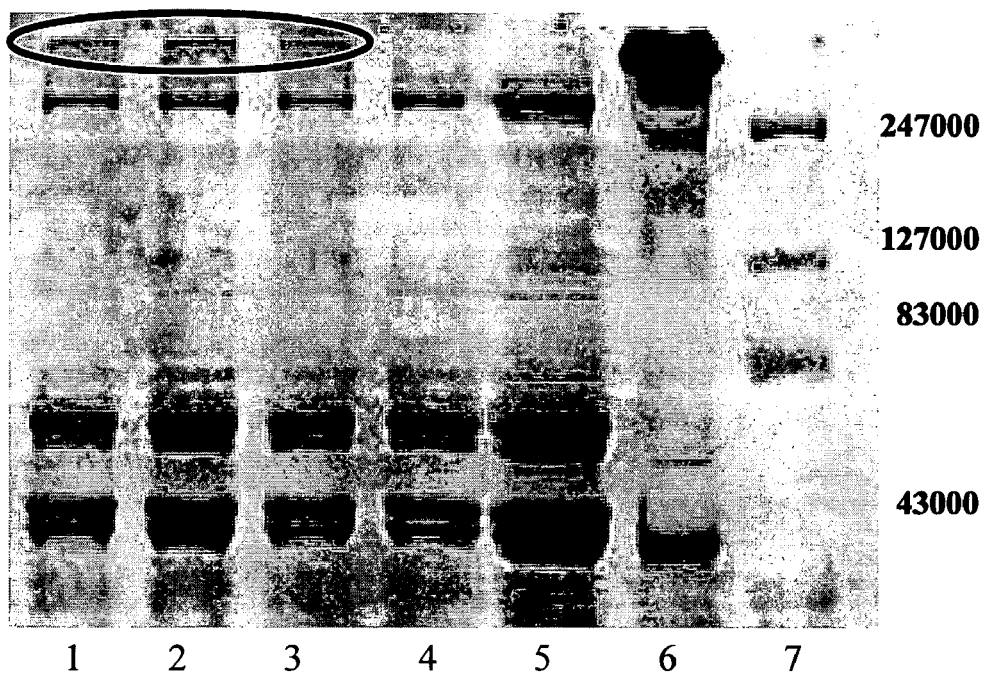
FIG. 1 is a photograph of SDS-PAGE in which the HA-fibrinogen conjugate was assayed. Lanes 1-3 represent reduced HA-fibrinogen conjugate; lane 4 represents reduced unconjugated mixture of HA and fibrinogen; lane 5 represents reduced fibrinogen; lane 6 represents unreduced fibrinogen; lane 7 represents molecular weight markers.

The present invention provides water-soluble reactive esters of carboxy polysaccharides useful in the preparation of polysaccharide-fibrinogen conjugates and to methods of preparing same. The hitherto known preparation of carboxy polysaccharide active esters require the use of dipolar aprotic solvents, for example the preparation of HA active esters in N-methylpyrrolidone disclosed in U.S. Pat. No. 5,856,299. The preparation of N-hydroxysuccinimide ester of HA in dimethylsulfoxide was described by Luo and Prestwich (2001). In aqueous solutions, carboxypolysaccharides are usually activated by carbodiimides in a "one-pot" reaction in the presence of the nucleophile to be conjugated. This "one pot" reaction has adverse features since the carbodiimide activator reacts with the nucleophile to produce a multiplicity of side products, especially if the nucleophile is a multifunctional molecule such as a polypeptide.

The present invention provides novel methods for preparing water-soluble carboxy polysaccharide active esters. These active esters are prepared in a two-step procedure wherein the activator (e.g. carbodiimide) is removed from the solution following the first step of the reaction. The resulting active ester, which is substantially free of an activator, is chemically conjugated with fibrinogen thus producing water-soluble polysaccharide-fibrinogen conjugate without the formation of undesired side products. The water-soluble conjugates of the present invention are produced in high yields and can be found useful in a plurality of clinical applications.

The present invention further provides carboxy polysaccharide-fibrinogen conjugates suitable for the preparation of fibrin clots or fibrin matrices for tissue repair and tissue engineering. The fibrin(ogen) containing adhesives, clots or scaffolds disclosed here for the first time possess many advantageous properties over those of known products. Advantages of the products of the present invention include:

biocompatible, non-immunogenic natural product;

serum stable composition;

useful in tissue repair and tissue engineering applications including as a component for the preparation of a tissue adhesive, clot or implant;

may be formulated for controlled release of bioactive agents;

excellent cell bearing properties including cell attachment, cell distribution and cell viability throughout clot or implant.

DEFINITIONS

For convenience and clarity certain terms employed in the specification, examples and claims are described hereinbelow.

"Carboxy polysaccharide" as used herein refers to complex carbohydrates composed of monosaccharides joined by glycosidic bonds and having at least one carboxyl group. The term "carboxy polysaccharide" includes salts thereof, such as sodium or potassium salts, alkaline earth metal salts such as calcium or magnesium salts. Carboxy polysaccharide further includes glycosaminoglycans and anionic polysaccharides. Non-limiting examples of anionic polysaccharides include, but are not limited to, alginate, galactans, galactomannans, and glucomannans.

A "glycosaminoglycan" or "GAG" as used herein refers to a long unbranched polysaccharide molecules found on the cell surface or extracellular matrix. Non-limiting examples of glycosaminoglycan include, but are not limited to heparin, chondroitin sulfate, dermatan sulfate, heparan sulfate, keratan sulfate, hyaluronic acid, and their salts, including low molecular weight forms of the glycosaminoglycans are intended to be included within the scope of the invention.

The term "reactive carboxy polysaccharide" refers to a polysaccharide in which at least part of the carboxy functional groups have been modified into a reactive functionality, for example an active ester, an anhydride, etc.

"Active esters" or "active ester functional groups" refer to carboxy moieties of a polysaccharide chemically treated to form a "reactive" ester having higher reactivity with nucleophiles than the corresponding carboxylic acid functionality. Alcohols suitable as esterifying components of the carboxy groups according to the present invention include, but are not limited to, aromatic alcohols, substituted aromatic alcohols, aromatic heterocyclic alcohols, substituted aromatic heterocyclic alcohols, N-hydroxylamine, or a combination thereof. In some embodiments, the alcohol is N-hydroxylamine selected from the group consisting of N-hydroxysuccinimide and sulfo-N-hydroxysuccinimide.

A preferred carboxylated polysaccharide is hyaluronic acid (HA) and its derivatives including but not limited to, its partial esters with aliphatic, aryliphatic, heterocyclic and cycloaliphatic alcohols. Salt derivatives of HA including, but not limited to, sodium salts, quaternary ammonium salts and the like, are considered within the scope of the present invention as well. Suitable molecular weights of hyaluronic acid and its partial esters range from about $10^4$ Daltons to about three million ($3 \times 10^6$) Daltons.

A "water-soluble carbodiimide" refers to a carbodiimide preferably selected from the group consisting of (1-[3-(dimethylamino)propyl]-3-ethylcarbodiimide hydrochloride (EDC); (1-[3-(dimethylamino)propyl]-3-ethylcarbodiimide methiodide; and 1-cyclohexyl-3-(2-morpholinoethyl)carbodiimide metho-p-toluenesulfonate.

Water insoluble polymers include cation exchange resins such as Amberlite® IRC50 and Dowex®50 and resins including polystyrene, polyacrylates and the like.

As used herein, the singular forms "a," "an" and "the" include plural forms unless the context clearly dictates otherwise. Thus, for example, reference to "a carboxy polysaccharide" includes combinations of carboxy polysaccharides.

"Plasma" as used herein refers to the fluid, non-cellular portion of the blood of humans or animals as found prior to coagulation.

"Plasma protein" as used herein refers to the soluble proteins found in the plasma of normal humans or animals. These include, but are not limited to, coagulation proteins, albumin, lipoproteins and complement proteins. The major plasma protein is fibrinogen, which upon cleavage by thrombin in the presence of calcium ions and Factor XIII, is converted to fibrin. The plasma protein solution used for the preparation of the fibrin components of the present invention may be obtained from a commercial source, natural or recombinant proteins, or may be prepared from plasma. According to one embodiment, the plasma protein solution derives from allogeneic plasma. According to another embodiment, at least one of the components, preferably the plasma proteins used for preparing the matrix, derives from autologous plasma or recombinant proteins. According to another embodiment, all of the plasma components used in preparing the matrix are autologous. The plasma proteins may be isolated by a variety of methods, as known in the art and exemplified hereinbelow, resulting in a fibrin matrix having substantially similar properties, as measured by elasticity, compression and cell bearing capabilities. A stable thrombin component may be isolated from autologous plasma, according to methods known in the art, for example those disclosed in U.S. Pat. No. 6,274,090 and Haisch et al (2000).

Fibrinogen is the principal protein of vertebrate blood clotting. It is a hexamer containing two sets of three different chains ($\alpha$, $\beta$, and $\gamma$), linked to each other via disulfide bonds. The N-terminal sections of these three chains are evolutionary related and contain the cysteines that participate in the cross-linking of the chains. However, there is no similarity between the C-terminal part of the $\alpha$ chain and that of the $\beta$ and $\gamma$ chains. The C-terminal part of the $\beta$ and $\gamma$ chains forms a domain of about 270 amino-acid residues.

The fibrinogen as used in the present invention, can originate from any animal species including mammal and avian species, from a recombinant source, or total or partially purified plasma proteins. The fibrinogen component of the conjugate can be obtained by conventional methodology. Examples of such methods include centrifugation, cryo-precipitation and precipitation using polyethylene glycol, ether, ethanol, glycine or ammonium sulfate from plasma. Methods of obtaining suitable fibrinogen are disclosed, for example, in U.S. Pat. No. 5,290,918. According to one embodiment, fibrinogen includes fibrinogen variants, including the high molecular weight (HMW), the low molecular weight (LMW) and the LMW derivative (LMW') variants, for example as disclosed in PCT patent application WO 03/087160, the contents of which are incorporated by reference herein.

"Fibrin glue", also called fibrin adhesive or sealant, has numerous applications in the clinic. Generally, fibrin glue is liquid or semisolid until it is admixed with a fibrinogen cleaving agent, for example thrombin, which converts the fibrinogen to fibrin monomers, which are water insoluble.

A "fibrin clot", also interchangeably referred to a plasma protein clot or a fibrin membrane, refers to a semisolid or solid mass of fibrin generated from the action of a protease such as thrombin, on fibrinogen. A fibrin clot can be generated in situ or ex vivo and can serve for tissue replacement, tissue repair and for attachment of cells. A "porous fibrin matrix" or interchangeably a "porous fibrin scaffold" is prepared by freeze-drying of the fibrin clot of the present invention. The terms "lyophilize" or "freeze drying" refer to the preparation of a composition in dry form by rapid freezing and dehydration in the frozen state (sometimes referred to as sublimation). This process may take place under vacuum at reduced air pressure resulting in drying at a lower temperature than required at full pressure. U.S. Pat. No. 7,009,039 to one of the inventors of the present invention, teaches porous plasma protein matrices useful in tissue repair.

The term "stable fibrin clot" as used herein refers to the ability of a fibrin clot to resist degradation by serum proteases in vitro for at least one week at 37° C. The fibrin clot prepared using HA-fibrinogen conjugate (HA-conjugated) according to the principles of the present invention was shown to be more stable to both serum proteases and degradation by urea, than a fibrin clot prepared from a mixture of HA and fibrinogen (HA-unconjugated).

The term "HA-conjugated fibrin clot" refers to a clot which is formed from HA-fibrinogen conjugate of the present invention, by the addition of a fibrinogen cleaving agent such as thrombin. Similarly, the terms "heparin-conjugated fibrin clot" and "CMC-conjugated fibrin clot" refer to clots which are formed from heparin-fibrinogen and carboxymethylcellulose-fibrinogen conjugates of the present invention respectively, by the addition of a fibrinogen cleaving agent such as thrombin. The term "HA-unconjugated fibrin clot" refers to a clot which is formed from a mixture of HA and fibrinogen by the addition of a fibrinogen cleaving agent such as thrombin.

A "polypeptide" refers to an amino acid sequence which can be selected from an oligopeptide, a peptide, or protein sequence, and variants and fragments thereof, and to naturally occurring, synthetic or recombinant molecules. The term polypeptide as used herein is not meant to limit the polypeptide to the complete, wild type amino acid sequence associated with the recited protein molecule.

The term "biocompatible" as used herein refers to materials, which have low toxicity, clinically acceptable levels of foreign body reactions in the living body, and affinity with living tissues.

The term "cell-bearing" as used herein refers to the capacity of the clot to retain cells within its structure. In one embodiment, the cells are able to undergo proliferation and/or differentiation.

The term "implantation" refers to the insertion of a solid or semisolid composition of the invention into a patient, whereby the implant serves to replace, fully or partially, tissue that has been damaged, diseased or removed. Semi-solid or solid forms for implantation include, but are not limited to, sheets, tubes, membranes, sponges, flakes, gels, beads, microspheres, microparticles and the like.

The "biologically active" or "bioactive agents" incorporated into the compositions of the present invention, for example, growth factors, platelet and platelet extracts, angiogenic factors, and the like, are advantageous to, in non-limiting examples, promote a more rapid growth or differentiation of the cells within the implant, or alternatively promote a more rapid vascularization of the implant. Such factors were shown to be inherent to the compositions and form a source, or depot, of bioactive agent, for sustained release. Other bioactive agents include antibiotics, enzymes, additional plasma proteins or mixtures thereof.

The term "cartilage" as used herein, refers to a specialized type of connective tissue that contains chondrocytes embedded in an extracellular matrix. The biochemical composition of cartilage differs according to type but in general comprises collagen, predominantly type II collagen along with other minor types, e.g., types IX and XI, proteoglycans, other proteins and water. Several types of cartilage are recognized in the art, including, for example, hyaline cartilage, articular cartilage, costal cartilage, fibrous cartilage (fibrocartilage), meniscal cartilage, elastic cartilage, auricular cartilage, and yellow cartilage. The production of any type of cartilage is intended to be within the scope of the invention. The term "chondrocytes" as used herein, refers to cells that are capable of producing components of cartilage tissue.

Extracellular matrix proteins refer to polypeptides, peptides, glycoproteins that are found within or make up the extracellular matrix of tissue. Exemplary proteins include the many different types of collagen including collagen I, collagen II, collagen, vitronectin, fibronectin, elastin, laminin.

The present invention relates in one aspect to water-soluble conjugates of carboxy polysaccharides and fibrinogen. The compositions and methods of the present invention are effective for applications in vivo and in vitro including biocompatible implants for tissue engineering as well as in biotechnology. The conjugates are especially useful in the preparation of compositions useful in tissue regeneration and repair including fibrin glue and three-dimensional tissue repair matrices, such as fibrin clots or porous fibrin scaffolds.

Fibrin glue is typically rapidly degraded in the body by tissue and plasma resident proteases. The polysaccharide-fibrinogen conjugates of the present invention provide compositions, which are more resistant to enzymatic degradation.

In one embodiment, the present invention relates to a conjugate comprising a carboxy polysaccharide and fibrinogen which is particularly useful in the preparation of fibrin adhesives, fibrin clots and freeze-dried fibrin matrices.

The stable fibrin clot of the invention may be used per se, comprising a conjugate comprising a carboxy polysaccharide and fibrinogen or a fragment thereof for clinical and biotechnological applications. It may however, further comprise additives that impart other advantageous biological, physical and mechanical characteristics to the composition. Copending international patent application WO 03/007873 of one of the inventors of the present invention, discloses a fibrin matrix or sponge comprising plasma proteins and at least one anti-fibrinolytic agent, optionally further comprising agents such as polysaccharides, anionic polysaccharides, glycosaminoglycans, or semi-synthetic and synthetic polymers added in the preparation to improve certain physical, mechanical and biological properties of the matrix. The incorporation of at least one such agent was shown to impart superior characteristics including elasticity and regular pore size to the sponge. The present invention now provides a soluble conjugate of a carboxy polysaccharide and fibrinogen, thereby obviating the need for additives.

Bioactive Agents

In one embodiment, the composition of the invention further comprises at least one bioactive agent, such as a cytokine, a growth factor and their activators, platelets, a bioactive peptide etc. Without wishing to be bound by theory or mechanism of action, incorporation of such agents into the adhesive, clot or freeze dried matrix of the present invention provides a slow-release or sustained-release mechanism from the composition. As the composition degrades in vivo, the bioactive agents are released into the surrounding milieu. For example, growth factors, structural proteins or cytokines which enhance the temporal sequence of wound repair, enhance angiogenesis, alter the rate of proliferation or increase the metabolic synthesis of extracellular matrix proteins are useful additives to the compositions of the present invention.

The bioactive proteins of the invention, are polypeptides or derivatives or variants thereof, obtained from natural, synthetic or recombinant sources, which exhibit the ability to stimulate DNA synthesis and cell division or differentiation of a variety of cells, including but not limited to, primary fibroblasts, embryonal stem cells (ESC), adult stem cells, chondrocytes, vascular and corneal endothelial cells, osteoblasts, myoblasts, smooth muscle and neuronal cells. Representative proteins include bone growth factors (BMP2, BMP4, BMP7 and IGF1) and fibroblast growth factors for bone and cartilage healing. The fibroblast growth factors include, but are not limited to, FGF1, FGF2, FGF4, FGF9 and FGF18 and their variants including FGF2(3,5Q)N111G of copending international application WO 03/094835 of one of the inventors. Other proteins that can be used as bioactive agents include, but are not limited to, cartilage growth factor genes (CGF, TGF-β) for cartilage healing, nerve growth factor genes (NGF), and certain FGFs for nerve healing. Additionally, general growth factors such as platelet-derived growth factor (PDGF), vascular endothelial growth factor (VEGF), insulin-like growth factor (IGF-1), keratinocyte growth factor (KGF), endothelial derived growth supplement (EDGF), epidermal growth factor (EGF) and other proteins which may enhance the action of the growth factors are within the scope of the present invention. The term "variants" refers to polypeptides having at least one amino acid substitution, deletion or addition. Preferred variants exhibit at least one property selected from enhanced stability, enhanced activity or increased receptor specificity, when compared to the counterpart wild type polypeptide.

According to one embodiment of the present invention, the at least one bioactive agent is a therapeutic protein selected from the group consisting of growth factors and their variants. In one embodiment, the growth factor is a fibroblast growth factor (FGF) or FGF variant having the capacity to induce cartilage and bone repair and regeneration and/or angiogenesis. The growth factors may be incorporated at a wide range of concentrations, depending on the application.

Additionally, cells genetically engineered to express the aforementioned proteins are encompassed by the present invention.

Other biologically active agents that may be included into the conjugate composition include blood platelets, platelet supernatants or extracts and platelet derived proteins, hormones, chemotherapeutic agents, anti-rejection agents, analgesics and analgesic combinations, steroids, anti-inflammatory agents, adhesion proteins, anti-microbial agents or enzymes. Bioactive agents including platelets and platelet supernatant or extract, promote the proliferation and differentiation of various cell types. Bioactive agents belonging to the class of anti-microbial or anti-inflammatory agents may accelerate the healing process by minimizing infection and inflammation. Enzymes such as chondroitinase or matrix metalloproteinases (MMPs) may be incorporated to aid in the degradation of cartilage, thus stimulating release of cells into the matrix and the surrounding milieu. In one non-limiting example, the bioactive agent, added ab initio or at any stage following preparation, may be selected to enhance the healing process of the injured or diseased tissue.

Applications

The water-soluble activated carboxy polysaccharide may be used as a coating for diseased or damaged tissue, such as for in situ coating of articular cartilage. Without wishing to be bound to theory, the soluble activated carboxy polysaccharide is injected to the surface of an osteoarthritic joint, thereby coating the joint with a lubricant that can react with the polypeptides located therein. The soluble activated carboxy polysaccharide can also be used to coat a synthetic surface, for example that of a medical device including prosthesis. Cosmetic applications such as wrinkle smoothing applications, tissue augmentation and tissue bulking are within the scope of the present invention as well.

Additionally, the soluble carboxy polysaccharide-fibrinogen conjugate of the present invention is useful in the preparation of liquid, semi-solid and solid preparations for tissue engineering applications. It is within the scope of the present invention that said preparations include, but are not limited to, suitable use of molds, and/or compression, and/or drying, and/or lyophilization and/or any other method known in the art thus providing semi-solid or solid forms in any desired shape. Additionally, any form of injectable preparation including but not limited to injectable and non-injectable suspensions of particles, microspheres, microparticles of any desired size and shape might be used and is considered to be part of the present invention. It is noteworthy, that the products of the present invention may be further processed and/or treated and/or modified by subjecting said products to further treatment and/or one or more processing steps. Such treatments and/or modifications may include, but are not limited to, drying, freeze-drying, dehydration, critical point drying, molding into a mold, sterilization, homogenization (to modify and improve flow properties and injectability), mechanical shearing (to modify rheological properties and ease of injection), irradiation by ionizing radiation or electromagnetic radiation, mixing with pharmaceutically acceptable vehicle (for forming an injectable preparation for tissue bulking, and/or tissue augmentation and/or other purposes), sterilization by thermal means (autoclaving and the like), sterilization by chemical means (such as, but not limited to, sterilization using hydrogen peroxide, ozone, ethylene oxide and the like), and impregnation with an additive.

Furthermore, any suitable combinations of the above disclosed additional treatments or processing steps as well as other processing steps well known in the art may be used, in any suitable sequence, to provide any desired modified and/or dried, and/or shaped products of the present invention. It is however to be understood, that all of the abovementioned preparations are in accordance with the principles of the present invention excluding preparation which chemically or thermally alter the desired functionalities of products of the present invention.

The covalent interaction between the hyaluronic acid and fibrinogen provides a compound which is unexpectedly stable, is easy to manipulate and is useful in different clinical applications.

The in vivo uses of the conjugate are manifold. The fibrin adhesive comprising the water-soluble polysaccharide-fibrinogen conjugate may be provided as a dry preparation or an aqueous preparation. In some embodiments, the aqueous preparation is an aerosol formulation.

In one embodiment, the fibrin adhesive has utility as a coating on synthetic or other implants such as pins and plates, for example, in hip replacement procedures. Thus, the present invention further provides implants or medical devices coated with the fibrin adhesive of the invention.

In a surgical procedure, the fibrin adhesive may be used as an adjunct to control bleeding or leakage of air and other bodily fluids. Additional applications of fibrin adhesive include closure of bronchopleural fistulas, reduction of hemorrhage in cardiac surgery and eliminate cerebrospinal fluid leakage in neurosurgery. The adhesive is also useful for the slow release of drugs, for example antibiotics at the infection site, growth factors to organs preferably bone and cartilage and chemotherapy to tumors.

In yet further embodiments of the invention, the fibrin glue may be utilized as coating of synthetic or other implants or medical devices. The glue of the invention may be applied to prostheses, such as pins or plates, by coating or adhering methods known to persons skilled in the art. The coating, which is capable of supporting and facilitating cellular growth, can thus be useful in providing a favorable environment for the implant or prosthesis.

The HA-fibrinogen conjugate can also be mixed with various cells and injected in vivo to the site of injury or disease together with a thrombin solution or any other fibrinogen-cleaving agent, to form a clot. The resulting fibrin clot exhibits advantageous properties including biocompatibility, stability and ability to be molded or cast into definite shapes. The latter is of particular importance since adapting the exact shape of the injured or defected site leads to more superior clinical outcomes.

The stable fibrin clot may be used as an implant per se, for providing mechanical support to a defective or injured site in situ and/or for providing a matrix within which cells from the defective or injured site proliferate and differentiate. The cells may be stem cells or progenitor cells or may be specialized cells such as, but not limited to, chondrocytes, osteoblasts, hepatocytes, or mesenchymal, endothelial, epithelial, urothelial, endocrine, neuronal, pancreatic, renal or ocular cell types.

The stable fibrin clot of the present invention may be used for the delivery of cells in situ to a specific site in the body. According to another embodiment, the clot is useful for implantation of cells into a specific site in the body. The cells may be mixed with the HA-fibrinogen conjugate prior to the formation of the clot, thus being encapsulated within the clot. Alternatively, the cells can be grown on the surface of the clot. Examples of cells that can be delivered and/or implanted include, but are not limited to, chondrocytes in patients with damaged or diseased cartilages. In addition, other cell types that can also be delivered are pluripotent or lineage uncommitted cells, such as stem cells, embryonic stem cells and mesenchymal stem cells. Lineage uncommitted cells are cells which are potentially capable of an unlimited number of mitotic divisions. These cells produce progeny cells with the capacity to differentiate into any cell type that can be grown either within or on the surface of the clot of the invention. In addition, other cell types that can be delivered are lineage committed "progenitor cells". Lineage committed "progenitor cells" are generally considered to be incapable of an unlimited number of mitotic divisions and will eventually differentiate into a specific cell type. Cell types to which lineage committed "progenitor cells" might differentiate include, but are not limited to, chondrocytes, osteoblasts, hepatocytes, or mesenchymal, endothelial, epithelial, urothelial, endocrine, neuronal, pancreatic, renal or ocular cell types.

Additionally, the cell of interest may be engineered to express a gene product which would exert a therapeutic effect, for example anti-inflammatory peptides or proteins, growth factors having angiogenic, chemotactic, osteogenic or proliferative effects. A non-limitative example of genetically engineering cells useful for enhancing healing is disclosed in U.S. Pat. No. 6,398,816.

Alternatively the stable fibrin clot may be freeze dried to generate a fibrin matrix for utilization in reconstructive surgery methods for regenerating and/or repairing tissue that have been damaged for example by trauma, surgical procedures or disease. The present invention provides a matrix for use as an implantable scaffold per se for tissue regeneration. According to one embodiment of the invention, the matrix serves as both a physical support and an adhesive substrate for in vivo cell growth. As cell populations grow and function normally, they begin to secrete their own extracellular matrix (ECM) support. According to another embodiment, the matrix may also be used for the delivery of cells in situ to a specific site in the body.

Scaffold applications include the regeneration of tissues such as neuronal, musculoskeletal, cartilaginous, tendonous, hepatic, pancreatic, renal, ocular, arteriovenous, urinary or any other tissue forming solid or hollow organs. Some typical orthopedic applications include joint resurfacing, meniscus repair, non-union fracture repair, craniofacial reconstruction or repair of an intervertebral disc.

A person skilled in the art will adjust the procedures exemplified below in accordance with specific tissue requirements. For example, for cartilage repair, the stable fibrin clot of the invention may be used in conjunction with other therapeutic procedures including chondral shaving, laser or abrasion chondroplasty, and drilling or microfracture techniques.

In the reconstruction of structural tissues like cartilage and bone, tissue shape is integral to function, thus requiring the molding of the matrix into three dimensional configuration articles of varying thickness and shape. Accordingly, the fibrin clot of the invention may be formed to assume a specific shape including a sphere, cube, rod, tube or a sheet. The shape is determined by the contour of a mold, receptacle or support which may be made of any inert material and may be in contact with the composition comprising the conjugate on all sides, as for a sphere or cube, or on a limited number of sides as for a sheet. The composition comprising the conjugate may be shaped in the form of body organs or parts and constitute prostheses.

Yet another aspect of the present invention provides methods of treatment and use of the stable fibrin clot of the invention for treating injured or traumatized tissue, including cartilage and bone defects. In another aspect, the present invention provides use of freeze-dried porous fibrin matrices of treating injured or traumatized tissue, including cartilage and bone defects. The methods of treatment described herein are advantageous in that they require minimal preparation for use by the medical practitioner. The in vivo uses of the porous fibrin matrix are manifold: First, as a scaffold for implant per se, thus providing mechanical support to a defective or injured site in situ and/or for providing support for cells from the defective or injured site to proliferate and differentiate. Second, the stable fibrin matrix of the invention, being an effective scaffold, supporting cell growth, may be utilized in vivo in reconstructive surgery, for example as a scaffold for regenerating cells and tissue including neuronal cells, cardiovascular tissue, urothelial cells and breast tissue. Some typical orthopedic applications include joint resurfacing, meniscus repair, non-union fracture repair, craniofacial reconstruction, osteochondral defect repair or repair of an intervertebral disc.

The fibrin clot or matrix of the invention may also be used in conjunction with other therapeutic procedures including chondral shaving, laser or abrasion chondroplasty, and drilling or microfracture techniques. Other uses include the treatment of defects resulting from disease such as osteoarthritis. The components of the clot may be cast into a mold specifically designed for a distinct lesion or defect. In a non-limiting example, the mold may be prepared by computer-aided design. In other instances, the medical practitioner may have to cut or slice the clot or matrices to fit a particular lesion or defect. The fibrin compositions of the present invention are particularly beneficial for minimally invasive surgical techniques such as a mini-arthrotomy or arthroscopies thus overcoming the need for fully open joint surgery.

Conjugate Chemistry

The conjugation of carboxy polysaccharides with nucleophiles has been hitherto performed in a "one pot" reaction in which the carboxylic functional groups of the carboxy polysaccharide are activated for nucleophilic attack in the presence of the nucleophile. The activation of the carboxylic functional groups is performed by reaction with a mixture of an activator, e.g. carbodiimide, and an appropriate alcohol, e.g. NHS, to form an active ester in situ, which further reacts with the nucleophile. In order to ensure a high degree of activation it is common practice to use an excess of carbodiimide. Usually, the molar ratio of carbodiimide to the carboxylic functional groups ranges between 2:1 to about 4:1. However, the presence of carbodiimide in the reaction may lead to an extremely impure conjugate due to side reactions with the nucleophile, especially if the nucleophile is a multi-functional compound such as a protein or polypeptide.

Since proteins and polypeptides carry functional groups e.g. carboxyl and thiol, which are reactive towards carbodiimides, their conjugation in a "one pot" procedure will always lead to the concomitant formation of intermolecular cross linked oligomers as well as intramolecular modified monomers.

The present invention discloses for the first time, that in order to overcome the undesirable side reactions, it is necessary to remove excess activator (carbodiimide) from the conjugation reaction and thus consequently perform a two-step conjugation procedure. In the first step, a reactive ester of a carboxy polysaccharide is formed in aqueous solution, from which the excess activator is completely removed. The solution is preferably pH controlled using a buffer. Following the first step of the reaction, an aqueous solution of carboxy polysaccharide active ester which is substantially free of the activator, is provided for use according to the principles of the present invention. In the second step, the reactive ester is reacted with the nucleophile, namely fibrinogen.

Method for the Preparation of a Reactive Water-Soluble Carboxy Polysaccharide

The present invention provides a method for preparing a reactive water-soluble carboxy polysaccharide wherein at least part of the carboxy groups are modified into active ester functional groups, the method comprising the steps of:

a) providing an aqueous solution comprising at least one carboxy polysaccharide;

b) modifying at least part of the carboxy functional groups of the carboxy polysaccharide to active ester functional groups in the presence of at least one water-soluble activator and an alcohol;

c) removing residual activator from the solution of the water-soluble reactive polysaccharide.

In certain embodiments, the reaction for the preparation of a reactive ester is performed in a buffered solution having a pH range of 4-8. In a preferred embodiment, the reaction is performed in a solution having pH 5-6. According to some embodiments, the molar ratio between the carbodiimide and the carboxy functional groups of the carboxy polysaccharide is about 1:1 to about 8:1. In certain preferred embodiments, the molar ratio is about 2:1 to about 4:1.

In some embodiments, the molar ratio between the alcohol and the carbodiimide is between about 1:1 to about 5:1. In a preferred embodiment, the weight ratio is about 1.6:1 to about 1:1.

In some embodiments, removal of the residual activator is achieved by adding water insoluble resin having affinity to said activator to reaction step b). The water insoluble resin can carry a functional group that chemically reacts or ionically interacts with the activator. The functional group is selected from a carboxy, phosphate and sulfate group. A preferred functional group is carboxy. Without wishing to be bound to theory or mechanism of action, the residual activator e.g. carbodiimide, is removed in order to prevent subsequent inter- and intra-molecular chemical reactions.

According to one embodiment, at least 80% of the residual activator is removed from the solution of the water-soluble reactive polysaccharide. In some embodiments, the water-soluble reactive polysaccharide solution is substantially free of the activator. The term "activator" refers to a condensing agent including, but not limited to, water-soluble carbodiimides selected from the group consisting of: (1-[3-(dimethylamino)propyl]-3-ethylcarbodiimide hydrochloride (EDC); (1-[3-(dimethylamino)propyl]-3-ethylcarbodiimide methiodide; and 1-cyclohexyl-3-(2-morpholinoethyl)carbodiimide metho-p-toluenesulfonate. Other carbodiimide compounds include, but are not limited to, N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide. Additional activators include, but are not limited to, carbonyl diimidazole (CDI), N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus compound (e.g. phosphorus oxychloride, phosphorous trichloride, etc.), thionyl chloride, oxalyl chloride, 2-ethyl-7-hydroxybenzisoxazolium salt, 2-ethyl-5-(m-sulfophenyl)isoxazolium hydroxide, (chloromethylene)dimethylammonium chloride,2,2,4,4,6,6-hexachloro-1,3,5,2,4,6-triazatriphosphorine, 1-benzensulphonyloxy-6-chloro-1H-benzotriazole, p-toluenesulfonyl chloride, isopropoxybenzenesulfoxyl chloride or the like; or a mixed condensing agent such as a mixture of triphenylphosphine and a carbon tetrahalide (e.g. carbon tetrachloride, carbon tetrabromide, etc.), a complex of N,N-dimethylformamide with phosphoryl chloride, phosgene or thionyl chloride or the like.

The term "substantially free of the activator" refers to an aqueous solution of reactive polysaccharide in which at least 90% of the residual activator is removed, and preferably at least 99% of the residual activator is removed.

Suitable alcohols within the scope of the present invention include, but are not limited to, aromatic alcohols, substituted aromatic alcohols, aromatic heterocyclic alcohols, substituted aromatic heterocyclic alcohols, N-hydroxylamine, or a combination thereof. In some embodiments, the alcohol is N-hydroxylamine selected from the group consisting of N-hydroxysuccinimide and sulfo-N-hydroxysuccinimide.

The water-soluble activated carboxy polysaccharide can be used per se. According to one aspect, the present invention provides water-soluble activated carboxy polysaccharides in an aqueous solution. The solution is preferably in a physiologically acceptable pH. According to another aspect, the water-soluble activated carboxy polysaccharide of the present invention can be used in the preparation of a water-soluble carboxy polysaccharide-fibrinogen conjugate.

The present invention further provides a method for the preparation of a carboxy polysaccharide-fibrinogen conjugate wherein the conjugate comprises an amide bond between a carboxylic functional group of the polysaccharide and an amino functional group of the fibrinogen, the method comprising the steps of:

a) providing an aqueous solution which is substantially free of the activator containing the water-soluble activated carboxy polysaccharide of the present invention;

b) providing an aqueous solution of fibrinogen;

c) mixing the water-soluble activated carboxy polysaccharide with the fibrinogen solution under conditions suitable for the formation of a water-soluble carboxy polysaccharide-fibrinogen conjugate;

d) purifying said water-soluble carboxy polysaccharide-fibrinogen conjugate.

In some embodiments, the reaction for the preparation of the carboxy polysaccharide conjugate is performed in a buffered solution of pH between 6-9. In a preferred embodiment, the reaction is performed at a pH ranging from 6.5 to 8.

A preferred conjugate of carboxy polysaccharide-fibrinogen is hyaluronic acid-fibrinogen conjugate.

In some embodiments, the hyaluronic acid (HA) has a molecular weight in the range of about $1\times10^4$ Daltons to about $3\times10^6$ Daltons. According to some embodiments, the weight ratio (w/w) of hyaluronic acid to fibrinogen is about 1:30 to about 5:1. In various embodiments, the weight ratio of HA to fibrinogen is about 1:25 to about 1:1. In specific embodiments, the weight ratio is about 1:24 to about 1:12. A currently most preferable weight ratio is about 1:24.

According to one aspect, the present invention provides a method for preparing a stable fibrin clot formed from water-soluble carboxy polysaccharide-fibrinogen conjugate comprising the following steps:

a) providing a thrombin solution and a solution comprising water-soluble carboxy polysaccharide-fibrinogen conjugate of the present invention;

b) admixing the thrombin solution and the conjugate solution in the presence of calcium ions;

c) incubating under conditions appropriate to achieving clotting.

In some embodiments, the carboxy polysaccharide of the polysaccharide-fibrinogen conjugate is hyaluronic acid, heparin or carboxymethyl-cellulose. According to one embodiment, the clot of the invention may be prepared by sequential introduction of the thrombin solution and conjugate solution into the mold or solid receptacle. Either solution may be introduced first. According to another embodiment, the thrombin solution and the conjugate solution are mixed together and subsequently introduced into a mold.

The fibrin clot may further comprise at least one bioactive agent or cells, added ab initio to either the thrombin solution or the conjugate solution, or to the mixture of both.

According to one embodiment, a conjugate solution comprising fibrinogen at a concentration of about 10 to about 50 mg/ml, is added to a thrombin solution to achieve formation of a clot. In other embodiments, the fibrin clot is formed in situ by injecting the fibrin adhesive and a thrombin solution to a wounded or diseased site.

It will be appreciated by those skilled in the art that the conjugates as well as fibrin clots and matrices described herein may be further modified by any chemical or biological modifiers known in the art. For example, some or all of the free functional groups remained in said products following their formation may be chemically or enzymatically treated to chemically introduce other chemical groups or moieties (such as, but not limited to, amino groups and/or carboxy groups, and/or hydroxyl groups, and/or nitro-groups, and/or halo groups, and/or haloacyl groups, and/or perhalo groups, and/or peroxo groups, and/or any other chemical groups or moieties the like) to further modify these groups to better control various properties of the products of the present invention. Exemplary modifications of the products of the invention include, but are not limited to, esterification of free hydroxyl or carboxy groups or acetylation of any free amino groups present on the polysaccharide backbone or on the protein (e.g. fibrinogen) backbone of the present invention. Such functional group modifications may be useful for further modifying the fine tuning of the conjugate/clot/matrix properties including, but not limited to, hydrophobicity, hydrophillicity, net charge at various selected pH levels, matrix porosity, matrix water absorbing capacity, resistance to enzymatic degradation and the like. The modifications might be tailored to desired applications. However, care should be exercised in the selection of the chemical groups being modified and in the nature of any chemical group which is being introduced to ensure a sufficient degree of biocompatibility as well as not to damage the desired functionality of the products.

The compositions of the present invention can be further mixed with excipients that are pharmaceutically acceptable and compatible with the active ingredient. Suitable excipients are, for example, water, saline, dextrose, glycerol, ethanol, or the like and combinations thereof.

In addition, if desired, the composition can contain minor amounts of auxiliary substances such as, but not limited to, pH buffering agents, which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, and the like.

The following examples are intended to be merely illustrative in nature and to be construed in a non-limitative fashion.

EXAMPLES

The following abbreviations are used in the examples, description and claims:
HA: sodium hyaluronate
EDC: 1-ethyl-3-[3-dimethylaminopropyl]carbodiimide hydrochloride
NHS: N-hydroxysuccinimide
PBS: phosphate buffered saline
MES: 2-(N-morpholino)ethanesulfonic acid
MOPS (3-(N-morpholino) propanesulfonic acid
DMEM: Dulbecco's modified Eagle's medium
SDS-PAGE: sodium dodecyl sulphate polyacrylamide gel electrophoresis
BSA: bovine serum albumin The HA used in the examples hereinbelow has a molecular weight of about $2.5 \times 10^5$ Dalton. The PBS used in the procedures hereinbelow, was purchased from Biological Industries IL (Cat No. 02-023-5A) and was diluted 1:10 for subsequent use. The fibrinogen used in the examples hereinbelow (excluding example 14) is purchased from Omrix Biopharmaceuticals Ltd. (IL). The FGF2 used in the examples hereinbelow is human FGF2 also known as bFGF, prostatin and heparin binding growth factor 2, having 155 amino acids.

Example 1

Attempts to Synthesize a Water-Soluble HA-Fibrinogen Conjugate

Two attempts to prepare a water-soluble conjugate of fibrinogen and HA were made following a "one pot" procedure or a two-step procedure. The first attempt was as follows:
EDC (6 mg, 0.031 mmols) and NHS (3.6 mg, 0.031 mmols) were added to a mixture of HA (4 mg, 0.01 mmols carboxylic groups) and fibrinogen (72 mg) in PBS (3 ml). The clear solution was gently rotated for 60 minutes at room temperature (RT). A heavy precipitate was obtained presumably, without being bound by any mechanism of action, due to a side reaction in which EDC cross-linked fibrinogen molecules as well as conjugate molecules intermolecularly.

A second unsuccessful attempt to prepare a water-soluble conjugate of fibrinogen and HA via a two-step reaction was made, as follows:
EDC (6 mg, 0.031 mmols) and NHS (3.6 mg, 0.031 mmols) were added to a solution of HA (4 mg) in water (1 ml). The clear solution was gently rotated at RT for 60 minutes after which it was mixed with a solution of fibrinogen (72 mg) in PBS (2 ml). The clear mixture was left at RT for 2 hours. A precipitate was obtained similarly to the first experiment.

Example 2

Removal of Residual EDC, Following Activation of HA

EDC (6 mg, 0.031 mmols) and NHS (3.6 mg, 0.031 mmols) were added to a solution of HA (4 mg) in 1.5 ml buffer MES (50 mM, pH 5.5). The clear mixture was gently rotated for 60 min. A water insoluble resin (Amberlite® IRC-50, Na⁺ form, 100 mg) was then added and the mixture was further rotated for 15 min. The resin was separated from the reaction mixture by centrifugation and the amount of EDC in the supernatant was determined following a published procedure (Gilles et al., 1990). The amount of EDC was found to be less than 0.2 µg/ml, which is the lowest detection limit of the above-mentioned procedure.

In a control experiment, in which no insoluble resin has been used, 1.13 mg/ml of EDC remained in the reaction mixture.

Example 3

Synthesis of a Water-Soluble Conjugate of Fibrinogen and HA Via a Two-Step Procedure Step 1: EDC (6 mg, 0.031 mmols) and NHS (3.6 mg, 0.031 mmols) were added to a solution of HA (4 mg, 0.01 mmols carboxylic groups) in 1.5 ml buffer MES (50 mM, pH 5.5). The clear mixture was gently rotated at RT for 60 minutes. The resin IRC-50 (Na⁺ form, 100 mg) was then added and the mixture was further rotated for 15 minutes, after which it was centrifuged for 30 seconds to separate the insoluble resin from the activated HA solution.

Step 2: The activated solution obtained in step 1, was added to a solution of fibrinogen (72 mg) in 1.5 ml buffer MOPS (200 mM, pH 7.5) and the clear reaction mixture was gently rotated for 2 hours. The soluble conjugate thus obtained was further purified by exhaustive dialysis against saline (0.9% NaCl). The conjugate solution of a final 2.8 ml volume, was stored at 4° C. and used as a stock solution for following experiments.

Example 4

Qualitative Proof for the Formation of HA-Fibrinogen Conjugate

The conjugate that was prepared according to example 3 was reduced under the following conditions: a conjugate sample was added to 1 ml of a reduction buffer composed of 4M urea, 1 mM EDTA, 50 mM DTT and PBS (pH 7). The mixture was then incubated for 1 hour at 37° C.

In parallel, a sample of unconjugated mixture of HA (4 mg) and fibrinogen (72 mg) as well as a sample of fibrinogen solution were reduced under exactly the same conditions. Each of the samples contained a calculated amount of 1 mg fibrinogen prior to reduction. Reduced samples (each generated from 1 μg fibrinogen) as well as unreduced fibrinogen (1 μg) were subjected to gel electrophoresis (7.5% SDS-PAGE).

As illustrated in FIG. 1, the reduced conjugate can be seen as an additional high molecular band (>300,000 Da). This band was not observed in the reduced unconjugated mixture of HA and fibrinogen nor in the reduced fibrinogen solution.

Example 5

Synthesis of Water-Soluble Fibrinogen Conjugates with Heparin and Carboxymethyl-Cellulose (CMC) Via the Two-Step Procedure A heparin-fibrinogen conjugate was prepared from 4 mg of heparin (Sigma; Cat No. H-5284; MW 6000 Da) and 72 mg of fibrinogen under the same conditions as described in example 3. The heparin-fibrinogen conjugate was purified by exhaustive dialysis against saline (0.9% NaCl) and was stored at 4° C.

A CMC-fibrinogen conjugate was prepared from 4 mg of carboxymethyl-cellulose (Sigma; Cat No. C-5678; MW 90,000 Da) and 72 mg of fibrinogen under the same conditions as described in example 3. The CMC-fibrinogen conjugate was purified by exhaustive dialysis against saline (0.9% NaCl) and was stored at 4° C.

Example 6

Preparation of HA-Conjugated Fibrin Clot

Preparation of the clot was performed by polymerizing the HA-fibrinogen conjugate with thrombin according to the following procedure: Thrombin solution (150 μl, 72 U) was evenly spread in a well of a polystyrene 6-well culture plate. A solution of the conjugate (72 mg) in saline (3 ml) was slowly added using a syringe. The mixture was rotated at 650 rpm for 3 minutes and further incubated at 37° C. for 2 hours, to yield a transparent and rigid gel.

Example 7

Preparation of Heparin-Conjugated and CMC-Conjugated Fibrin Clots

The heparin-fibrinogen conjugate which was prepared according to example 5, was polymerized similarly to the description in example 6, with the following exception: a ratio of 10 U thrombin to 1 mg conjugate was needed for an efficient clot formation, as compared to a ratio of 1 U thrombin to 1 mg conjugate in example 6. The clot was obtained as a transparent and rigid gel.

The CMC-fibrinogen conjugate, which was prepared according to example 5, was polymerised similarly to the description of the preparation of HA-conjugated fibrin clot (example 6). The clot was obtained as a transparent and rigid gel.

Example 8

Proteolytic Stability of HA-Conjugated, Heparin-Conjugated and CMC-Conjugated Fibrin Clots HA-conjugated fibrin clot was prepared from HA-fibrinogen conjugate (72 mg) as described in example 6. Heparin-conjugated fibrin clot was prepared from heparin-fibrinogen conjugate (72 mg) and CMC-conjugated fibrin clot was prepared from CMC-fibrinogen conjugate (72 mg) as described in example 7.

Control clots were prepared from unconjugated mixtures of the polysaccharides: HA, heparin or CMC (4 mg each) and fibrinogen (72 mg) in saline (3 ml). An additional control was prepared from fibrinogen (72 mg) and saline (3 ml) under the exact same conditions. Each clot was immersed in a culture medium (DMEM, 3 ml) containing 20% human serum and incubated at 37° C. The medium was replaced every other day.

The control clots that were prepared from fibrinogen alone or from a mixture of fibrinogen and a polysaccharide, were degraded and completely dissolved within 5 days. In contrast, the HA-conjugated fibrin clot demonstrated high stability and did not dissolve even after 3 weeks. Similarly, the heparin-conjugated fibrin clot as well as the CMC-conjugated fibrin clot were stable for at least 2 weeks.

Example 9

Stability of HA-Conjugated Fibrin Clot and HA-Unconjugated Fibrin Clot in Urea

The stability of a fibrin clot prepared from the water-soluble HA-fibrinogen conjugate (HA-conjugated) in urea was compared to a fibrin clot prepared from a mixture of HA and fibrinogen (HA unconjugated). An HA conjugated fibrin clot was prepared from the water-soluble HA-fibrinogen conjugate (5 mg) in saline (300 μl) as described in Example 6. A clot comprising an unconjugated mixture of HA (0.28 mg) and FBN (5 mg) in saline (300 μl) was prepared using the same conditions. The clots were immersed at room temperature in a solution of 10M urea, similar to a published procedure (McKee et al., 1970).

Figure 2:
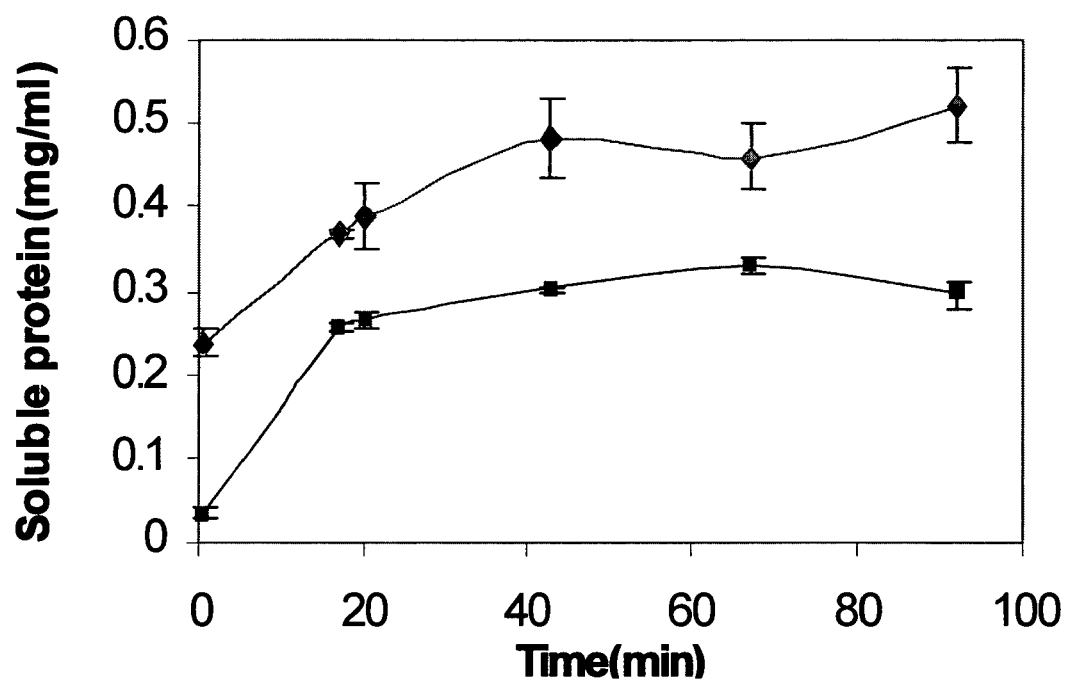
FIG. 2 provides a graph depicting the release in urea of soluble protein from HA-conjugated fibrin clot (square, lower line) and HA-unconjugated (diamond, upper line) fibrin clot.

Samples were collected at different time intervals and soluble protein was determined using the Bradford assay. As illustrated in FIG. 2, the clot prepared from the HA-fibrinogen conjugate of the present invention is significantly more stable in urea than its unconjugated HA counterpart.

Example 10

Modification of a Fibrin Clot with Activated HA Solution

A fibrin clot was prepared from fibrinogen (72 mg) and thrombin (72 U) in saline (3 ml) under the same conditions as described for the preparation of HA-conjugated fibrin clot (example 6). An activated HA solution was prepared from HA (4 mg) and EDC/NHS as described in example 3 (step 1).

The clot was immersed in the activated HA solution for 2 hours at room temperature after which it was rinsed with $H_2O$ (2 ml). Rinsing was repeated six times in order to ensure the removal of unbound HA. The covalently modified clot was consequently lyophilized at −20° C. for 24 hours (under 0.37 millibar) to yield a solid porous fibrin scaffold.

The scaffold was immersed in a culture medium (DMEM, 3 ml) containing 20% human serum and incubated at 37° C. The medium was replaced every other day.

Under these conditions, the modified scaffold demonstrated high stability and did not dissolve even after 3 weeks. In contrast, an unmodified solid porous fibrin scaffold which was treated under the exact same conditions, was degraded and completely dissolved within 7 days.

Example 11

HA-Conjugated Fibrin Clot is Compatible with Human Chondrocyte Proliferation A solution of HA-fibrinogen conjugate in saline (200 µl), which was prepared as described in example 3 from fibrinogen (5 mg) and HA (0.28 mg), was mixed with a suspension of human chondrocytes ($5 \times 10^4$ cells) in DMEM culture medium (10 µl). The mixture was polymerized as described in example 6. The clot was immersed in a culture medium (DMEM 0.5 ml) containing 20% human serum and incubated at 37° C. The medium was replaced every other day. After 5 days, the medium was removed and the clot was immersed in collagenase solution (280 U in 0.5 ml DMEM). After being incubated for 6 hours at 37° C., the clot disintegrated and completely dissolved thus releasing the cells into the solution.

It was found that the chondrocytes proliferated under the described conditions. Specifically, the number of chondrocytes was increased by four fold from $5 \times 10^4$ to approximately $2 \times 10^5$. The viability of the proliferated cells was found to be greater than 90%. The number of cells as well as their viability was determined using the Trypan blue exclusion method.

Example 12

Incorporation of FGF2 in HA-Conjugated and HA-Unconjugated Fibrin Clots Enhances Chondrocyte Proliferation The proliferation described in example 11 was shown to be further enhanced by incorporating growth factors in the clots. HA-conjugated clots, each containing human chondrocytes and FGF2 were prepared from HA-fibrinogen conjugate solutions (200 µl each) as described in example 11. The growth factor was added prior to the polymerization process. Each clot contained $5 \times 10^4$ cells and 0, 20 or 200 ng FGF2.

In parallel, HA-unconjugated clots, each containing the same amounts of HA and fibrinogen as in the HA-conjugated clots, were prepared as described in example 8. Each clot contained $5 \times 10^4$ cells and 0, 20 or 200 ng FGF2. The HA-conjugated and HA-unconjugated clots were incubated as described in example 11 and the cells were released into the medium after 3 and/or 5 days.

Figure 3A:
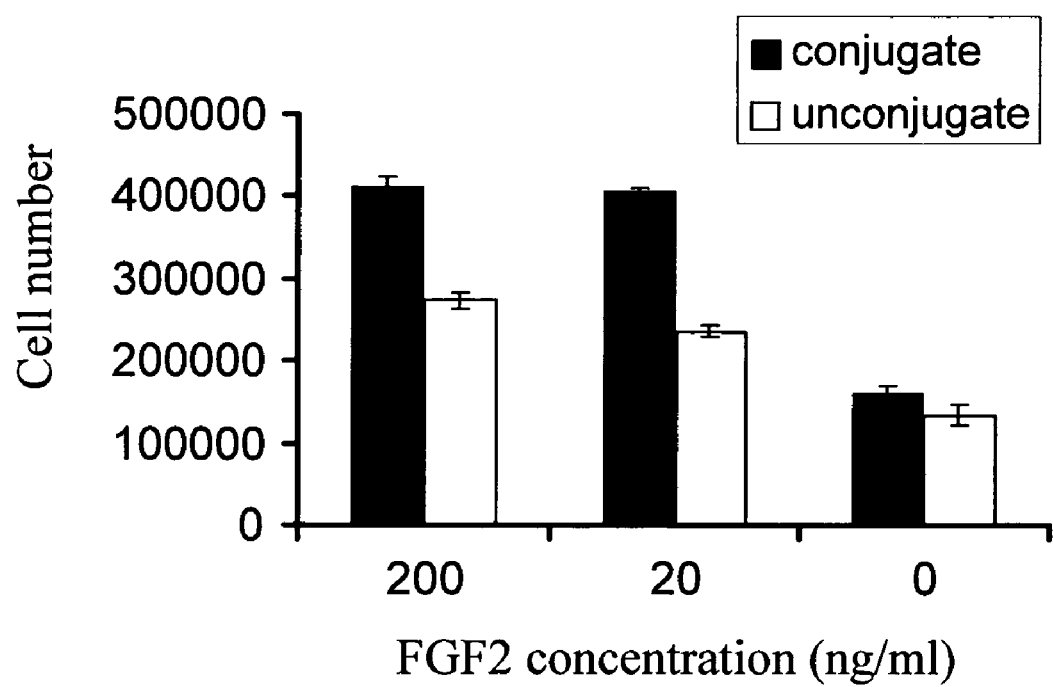
FIGS. 3A and 3B show cell proliferation following 3 and 5 days respectively. Proliferation was performed in HA conjugated and HA unconjugated fibrin clots further having varying concentrations of incorporated FGF2.
Figure 3B:
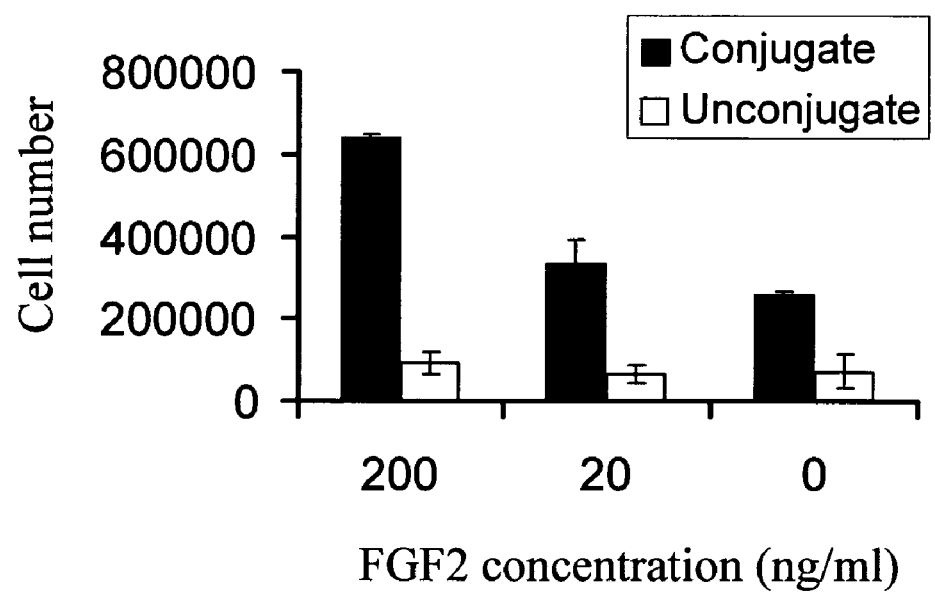

It was found that after 3 days of incubation, the cell number increased by around three fold in comparison to clots that did not contain FGF2. In the HA-unconjugated and the HA-conjugated clots which contained 20 or 200 ng FGF2, the cell number increased by four and eight fold respectively (FIG. 3A). After 5 days of incubation, the cell number in the HA-conjugated clot which contained 200 ng FGF2 was increased by approximately 12 fold (FIG. 3B). Under the same incubation conditions, the HA-unconjugated clots were disintegrated and completely dissolved in the culture medium. The viability of all the proliferated chondrocytes described in this example was found to be greater than 90%.

Example 13

Incorporation of FGF2 in HA-Conjugated Fibrin Clot and its Release from the Clot A HA-conjugated fibrin clot was prepared from a solution of HA-Fibrinogen conjugate in saline (200 µl) according to example 6. The conjugate solution was prepared from fibrinogen (5 mg) and HA (0.28 mg) according to example 3. FGF2 (35 µg) was added prior to the polymerization step. The FGF2 was released by gently agitating the clot at 37° C. with DMEM (1 ml, supplemented with 2% BSA). After an initial extraction for 1 hour, the release medium was replaced every 24 hours during the first week and every 48 hours during the following 2 weeks. The collected samples (1 ml each) were stored at −20° C. until measurement.

Figure 4:
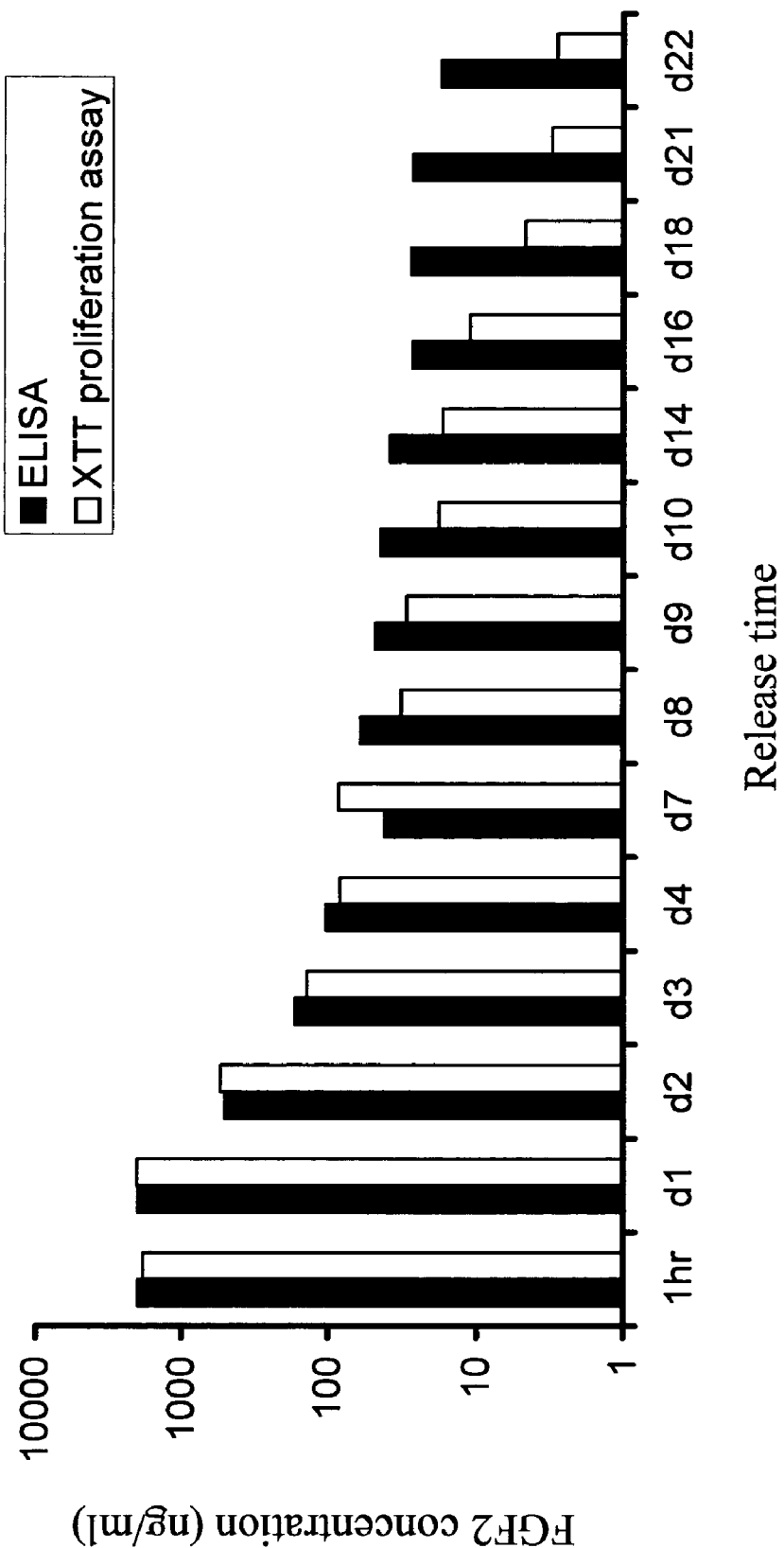
FIG. 4 shows the release of FGF2 from HA conjugated fibrin clot as measured by ELISA (Enzyme linked immunosorbent assay) vs. XTT proliferation assay.

The amount of the released FGF2 in each of the collected samples was measured using an FGF2 ELISA kit supplied by R&D Systems (Cat. No. DY 233) according to the manufacturer instructions. Its activity was determined using the XTT proliferation assay as described by Trudel et al. (2006). The release profile of FGF2 is illustrated in FIG. 4.

After a cumulative release time of 3 weeks, 14% (5 µg) of the incorporated FGF2 were found to be released. Additionally, during the first week the released FGF2 maintained full biological activity. Furthermore, even after 16 days most of the FGF2 activity was retained. The released levels of FGF2 were found to be well above their functional and physiological levels in biological systems.

Example 14

Characterization of HA-Conjugated Plasma Protein Clot

Proteolytic Stability

Human fibrinogen cryoprecipitated from entire human plasma (10 mg) was covalently conjugated to HA (0.56 mg) according to example 3. The conjugate solution had a final volume of 400 µl. A clot was prepared from a 200 µl sample according to example 6 except for thrombin being replaced by $CaCl_2$ solution (30 µl, 50 mM). The proteolytic stability of the clot in a culture medium containing human serum was examined as described in example 8. The clot was found to be stable for at least 3 weeks.

Compatibility with Human Chondrocyte Proliferation

A chondrcyte-containing clot was prepared from a conjugate solution (200 µl) as described above. A suspension of human chondrocytes ($5 \times 10^4$) in DMEM culture medium (10 µl) was added prior to the polymerization step. The clot was further treated as described in example 11. It was found that the cell number increased by six fold from $5 \times 10^4$ to around $3 \times 10^5$. The viability of the proliferated cells was found to be greater than 90%. The number of cells as well as their viability was determined using the Trypan blue exclusion method.

Example 15

Human Mesenchymal Stem Cells (MSCs) from Mononuclear Fraction of Bone Marrow can Proliferate in the HA Conjugated Fibrin Clot A solution of HA-fibrinogen conjugate in saline (40 µl), which was prepared according to example 3 from fibrinogen (1 mg) and HA (0.056 mg), was mixed with 8 µl suspension of mononuclear cell fraction containing approximately $20 \times 10^6$ cells that was prepared from crude human bone marrow by separation on ficoll gradient. The mixture was polymerized as described in example 6. The clot was immersed in law-glucose DMEM+20% human serum further containing FGF2 and incubated at 37° C. The medium was replaced twice a week. At either day 14 or day 21, the medium was removed and the clot was immersed in collagenase solution (340 U) in DMEM (200 µl) and incubated at 37° C. After 6 hours, the clot was disintegrated and completely dissolved thus releasing the cells into the medium.

The viability of the cells was measured by the Probidium Iodide (PI) staining method. The cells were analyzed by flow cytometry using double staining with anti-CD45 (marker for hematopoietic cells) and anti-CD105 (marker for MSCs). Typically, MSCs are CD45−/CD105+. Analysis was performed using FACSCalibar flow cytometer (BD) and CellQuest software. The viability of the cells at day 14 and day 21 was found to be 94% and 72%, respectively.

As illustrated in table 1 hereinbelow, the decrease in viability is due to death of hematopoeitic cells. In contrast, the percentage of MSCs at day 14 and day 21 was found to increase from 16% to 41%, respectively. The MSCs derived from mononuclear fraction of human bone marrow are thus shown to proliferate in the HA-conjugated fibrin clot. In addition, prolonged survival (at least up to 21 days) of various hematopoeitic cells in addition to the MSCs is demonstrated as well. These findings are distinct from the classical method for expansion of bone-marrow-derived MSCs where hematopoetic cells constitute less than 5% of the total cell population after approximately 10 days of culture.

TABLE 1

Bone marrow derived cells found in the HA-fibrinogen conjugate clot at day 14 and day 21.

| Cell type | CD 45 staining | CD 105 staining | Size | Granulation | Cell % at day 14 | Cell % at day 21 |
|---|---|---|---|---|---|---|
| Mesenchymal stem cells (MSCs) | − | + | Small | No | 16 | 41 |
| Hematopoetic cells subpopulation #1 (probably lymphocytes) | + | − | Small | No | 28 | 16 |
| Hematopoetic cells subpopulation #2 (probably monocytes) | + | − | Medium | Medium | 27 | 11 |
| Hematopoetic cells subpopulation #3 (probably activated monocytes) | + | + | Medium | Medium | 2 | 2 |

Example 16

HA Conjugated Porous Fibrin Matrix for Use in Tissue Repair and Regeneration

The HA conjugated porous fibrin matrix of the present invention may be used as a cell bearing membrane for tissue repair and regeneration. In one aspect, the cells are cultured in the matrix in vitro, prior to implantation. In another aspect, the matrix is seeded with cells immediately before implantation and the cells are allowed to proliferate in vivo.

Cartilage biopsies from fresh pig cartilage are sectioned into small pieces, approximately of 3-4 mm thick, washed aseptically with PBS and placed in a new tube containing 3 ml MEM medium. The cartilage may be obtained from any vertebrate species, and is preferably allogeneic or autologous.

Collagenase type II is diluted 1:5 and 1 ml is added to the cartilage pieces following gentle shaking of the mixture in 37° C. inside an incubator over night. When most of the sample is digested, the suspension is poured through sterile gauze to remove matrix debris and undigested material. The filtrate is centrifuged and washed twice to remove residual enzyme.

The number of cells is determined by a hemocytometer and viability is determined by Trypan blue exclusion. The cells are plated in 150 cm$^2$ tissue culture flasks in 30 ml of culture medium at a concentration of 5×10$^6$ cells/ml. Flasks are placed in a 37° C. incubator at 5% CO$_2$ atmosphere and 95% humidity. The culture medium is changed every three to four days. The cells adhere and become confluent following one-week incubation.

At confluence, the cell medium is removed and 3 ml of a trypsin-EDTA solution is added. An amount of 30 ml of MEM+FBS is added and the solution is centrifuged at 800 g for 10 minutes. The supernatant is removed, the pellet dispersed and the cells are counted. To create a cell-bearing matrix, 10$^2$-10$^6$ cells are seeded on the HA conjugated porous fibrin matrix of 9 mm in diameter and a thickness of 2 mm (approximately 0.2 cm$^3$). The membranes are placed in a 37° C. incubator for 1 hour and 1 ml of fresh medium is added to each. The medium is replaced with fresh medium and every few days the membranes are taken to cell proliferation and differentiation analysis.

The cell population grown on the above membranes is tested for several chondrocyte differentiation markers. One of several phenotypes expressed during chondrocyte differentiation is glycosaminoglycan (GAG) production. The presence of GAGs is identified in histological staining, using Alcian blue and quantitated using the DMB (3,3'-dimethoxybenzidine dihydrochloride) dye method.

Example 17

Application of Water-Soluble Reactive Carboxy Polysaccharides

The articular cartilage of osteoarthritis patients degenerates, leaving rough patches and crevices in the cartilage. The loss of the cartilage cushion causes friction between the bones, leading to pain and limitation of joint mobility.

The carboxy polysaccharide reactive esters of the present invention are used as lubricants for joints. A solution of a reactive hyaluronic acid derivative is prepared according to the procedure described in example 2. The carboxy HA reactive ester is injected intra-articularly into the synovial space to coat the damaged tissue, thereby providing a protective layer between the damaged cartilage and the overlaying bone.

The reactive HA derivative is suited per se for treatment in the operating room or clinics. As such, a kit is provided containing EDC+NHS in solid forms as a first ingredient, an aqueous solution of HA as a second ingredient and IRC50 insoluble polymer for extracting the activator as a third ingredient. In addition, the kit may further contain biocompatible buffer solutions for adjusting the pH to a physiological pH, as supplementary ingredients. The ingredients included in the kit are mixed and filtered to exclude the insoluble polymer thus providing an aqueous solution of the active HA derivative for subsequent use.

The active HA derivatives can also be used for cosmetic applications. Exemplary applications include but not limited to, wrinkle smoothing applications, tissue augmentation, tissue bulking and the like. The derivatives are preferably administered via injections wherein the active ingredients prepared from the kit are packaged in a suitable syringe and injected subcutaneously.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

REFERENCES

Bulpitt P and Aeschlimann D. 1999. New strategy for chemical modification of hyaluronic acid: Preparation of functionalized derivatives and their use in the formation of novel biocompatible hydrogels. *J. Biomed. Mater. Res.* 47:2, 152-169.

Gilles M A, Hudson A Q and Borders C L Jr. 1990. Stability of water-soluble carbodiimides and aqueous solution. *Anal. Biochem.* 184, 244-248

Haisch A, Loch A, David J, Prub A, Hansen R and Sittinger M. 2000. Preparation of a completely autologous biodegradable fibrin matrix for tissue engineering. *Med. Biol. Eng. Comput.* (*Cell Eng.*) 38:6, 686-89.

Itokazu M, Yamamoto K, Yang W Y, Aoki T, Kato N and Watanabe K. 1997. The sustained release of antibiotic from freeze-dried fibrin-antibiotic compound and efficacies in a rat model of osteomyelitis. *Infection.* 25:6, 359-363.

LeBoeuf R D, Raja R H, Fuller G M and Weigel P H. 1986. Human fibrinogen specifically binds hyaluronic acid. *J. Biol. Chem.* 261:27, 12586-12592.

LeBoeuf R D, Gregg R R, Weigel P H and Fuller G M. 1987. Effects of hyaluronic acid and other glycosaminoglycans on fibrin polymer formation. *Biochem.* 26:19, 6052-6057.

Li H, Liu Y, Shu X Z, Gray S D and Prestwich G D. 2004. Synthesis and Biological Evaluation of a Cross-Linked Hyaluronan-Mitomycin C Hydrogel. *Biomacromol.* 5:3, 895-902.

Luo Y and Prestwich G D. 2001. Hyaluronic Acid-N-Hydroxysuccinimide: A useful intermediate for bioconjugation. *Bioconj. Chem.* 12, 1085-1088.

McKee P A, Mattock P and Hill R L. 1970. Subunit structure of human fibrinogen, soluble fibrin, and cross-linked insoluble fibrin. *Proc. Nat. Acad. Sci.* 66, 738-744.

Pouyani T and Prestwich G D. 1994. Functionalized derivatives of hyaluronic acid oligosaccharides: Drug carriers and novel biomaterials. *Bioconj. Chem.* 5, 339-347.

Prestwich G D, Marecak D M, Marecek J F, Vercruysse K P and Ziebel M R. 1998. Controlled chemical modification of hyaluronic acid: Synthesis, applications, and biodegradation of hydrazide derivatives. *J. Cont. Release.* 53, 93-103.

Sakurai K, Miyazaki K, Kodera Y, Nishimura H, Shingu M and Inada Y. 1997. Anti-inflammatory activity of superoxide dismutase conjugated with sodium hyaluronate. *Glycoconj. J.* 14, 723-728.

Shu X Z, Ghosh K, Liu Y, Palumbo F S, Luo Y, Clark R A and Prestwich G D. 2004. Attachment and spreading of fibroblasts on an RGD peptide-modified injectable hyaluronan hydrogel. *J. Biomed. Mat. Res.* 68A:2, 365-375.

Trudel S, Stewart A K, Rom E, Wei E, Li Z H, Kotzer S, Chumakov I, Singer Y, Chang H, Liang S B and Yayon A. 2006. The inhibitory anti-FGFR3 antibody, PRO-001, is cytotoxic to t(4;14) multiple myeloma cells. *Blood.* 107: 10, 4039-4046.

The invention claimed is:

1. A carboxy polysaccharide-fibrinogen conjugate, wherein the conjugate is water soluble and comprises an amide bond between a carboxylic functional group of the polysaccharide and an amino functional group of the fibrinogen.

2. The conjugate according to claim 1, wherein the carboxy polysaccharide is selected from the group consisting of a natural carboxy polysaccharide, a synthetic carboxy polysaccharide, a semi-synthetic polysaccharide, and combinations thereof.

3. The conjugate according to claim 2, wherein the natural carboxy polysaccharide is a glycosaminoglycan selected from the group consisting of hyaluronic acid, heparin, heparan sulfate, chondroitin sulfate, dermatan sulfate, keratan sulfate, combinations, derivatives, and salts thereof.

4. The conjugate according to claim 3, wherein the natural carboxy polysaccharide is hyaluronic acid.

5. The conjugate according to claim 2, wherein the semi-synthetic carboxy polysaccharide is selected from the group consisting of carboxymethylcellulose and carboxyethylcellulose.

6. A pharmaceutical composition comprising a water-soluble carboxy polysaccharide-fibrinogen conjugate according to claim 1 and a pharmacologically acceptable carrier or excipient.

7. The pharmaceutical composition according to claim 6, which further comprises a bioactive agent.

8. The pharmaceutical composition according to claim 7, wherein said bioactive agent is a growth factor selected from a fibroblast growth factor and variants thereof.

9. A method of treating or repairing injured, diseased or traumatized tissue in a subject in need thereof comprising the step of applying the composition according to claim 6 to the site of injured, diseased or traumatized tissue, wherein the tissue is selected from the group consisting of cartilage, dermal, cardiac, bone, urothelial, endocrine, neuronal, pancreatic, renal, hepatic and ocular tissue types.

10. A carboxy polysaccharide-fibrin clot derived from a composition comprising the water-soluble carboxy polysaccharide-fibrinogen conjugate according to claim 1 and thrombin, thereby providing a carboxy polysaccharide-fibrin clot.

11. The clot according to claim 10, wherein the carboxy polysaccharide is a glycosaminoglycan selected from the group consisting of hyaluronic acid, heparin, heparan sulfate, chondroitin sulfate, dermatan sulfate, keratan sulfate, combinations, derivatives, and salts thereof; or wherein the carboxy polysaccharide is selected from the group consisting of carboxymethylcellulose and carboxyethylcellulose.

12. The clot according to claim 10 further comprising cells selected from stem cells, progenitor cells, chondrocytes, osteoblasts, hepatocytes, mesenchymal cell types, endothelial cell types, epithelial cell types, urothelial cell types, endocrinal cell types, neuronal cell types, pancreatic cell types, renal cell types and ocular cell types.

13. A pharmaceutical composition comprising a carboxy polysaccharide-fibrin clot according to claim 10 and a pharmaceutically acceptable carrier or excipient.

14. The pharmaceutical composition according to claim 13, which further comprises a bioactive agent of a growth factor selected from a fibroblast growth factor and variants thereof.

15. A method of treating or repairing injured, diseased or traumatized tissue in a subject in need thereof comprising the step of applying the composition according to claim 13 to the site of injured, diseased or traumatized tissue, wherein the tissue is selected from the group consisting of cartilage, dermal, cardiac, bone, urothelial, endocrine, neuronal, pancreatic, renal, hepatic and ocular tissue types.

16. A porous fibrin matrix comprising a carboxy polysaccharide-fibrin clot derived from a composition comprising the water-soluble carboxy polysaccharide fibrinogen conjugate according to claim 1 and thrombin, thereby providing a porous fibrin matrix.

17. The fibrin matrix according to claim 16, wherein the carboxy polysaccharide is a glycosaminoglycan selected from the group consisting of hyaluronic acid, heparin, heparan sulfate, chondroitin sulfate, dermatan sulfate, keratan sulfate, combinations, derivatives, and salts thereof; or wherein the carboxy polysaccharide is selected from the group consisting of carboxymethylcellulose and carboxyethylcellulose.

18. A pharmaceutical composition comprising a porous fibrin matrix according to claim 16 and a pharmaceutically acceptable carrier or excipient.

19. The pharmaceutical composition according to claim 18, which further comprises a bioactive agent of a growth factor selected from a fibroblast growth factor and variants thereof.

20. A method of treating or repairing injured, diseased or traumatized tissue in a subject in need thereof comprising the step of applying the composition according to claim 18 to the site of injured, diseased or traumatized tissue, wherein the tissue is selected from the group consisting of cartilage, dermal, cardiac, bone, urothelial, endocrine, neuronal, pancreatic, renal, hepatic and ocular tissue types.

21. An aqueous solution comprising a N-hydroxysuccinimide carboxy polysaccharide active ester and fibrinogen, wherein the aqueous solution is substantially free of an activator.

22. A pharmaceutical composition comprising an aqueous solution of N-hydroxysuccinimide carboxy polysaccharide active ester according to claim 21, and a pharmaceutically acceptable excipient.

23. A method of treating or repairing injured, diseased or traumatized tissue in a subject in need thereof comprising the step of applying a pharmaceutical composition to the site of injured, diseased or traumatized tissue, wherein the tissue is selected from the group consisting of dermal, cardiac, cartilage, bone, urothelial, endocrine, neuronal, pancreatic, renal, hepatic and ocular tissue types, wherein the pharmaceutical composition is an aqueous solution comprising a N-hydroxysuccinimide carboxy polysaccharide active ester, being substantially free of an activator, and optionally containing a pharmaceutically acceptable excipient.

24. A method for the preparation of an aqueous solution comprising a N-hydroxysuccinimide carboxy polysaccharide active ester, wherein the aqueous solution is substantially free of an activator, and wherein part or all of the carboxy groups of the carboxy polysaccharide are modified into active ester functional groups, the method comprising the steps of:
providing an aqueous solution comprising at least one carboxy polysaccharide;
modifying part or all of the carboxy functional groups of the carboxy polysaccharide to active ester functional groups in the presence of at least one water soluble activator and a N-hydroxysuccinimide; and
removing residual activator from the solution of the water-soluble reactive polysaccharide.

25. An aqueous solution consisting essentially of a N-hydroxysuccinimide carboxy polysaccharide active ester formed by the method according to claim 24 and fibrinogen.

26. The clot according to claim 11, wherein the carboxy polysaccharide is a hyaluronic acid.

27. The clot according to claim 12, wherein the cells are mesenchymal cell types.

28. The method according to claim 20 for treating an orthopedic indication selected from the group consisting of joint resurfacing, meniscus repair, non-union fracture repair, craniofacial reconstruction, osteochondral defect repair or repair of an intervertebral disc.

29. A method of treating or repairing injured, diseased or traumatized tissue in a subject in need thereof comprising the step of applying a pharmaceutical composition comprising an aqueous solution of a carboxy polysaccharide active ester that is substantially free of an activator, and a pharmaceutically acceptable excipient to the site of injured, diseased or traumatized tissue, wherein the tissue is selected from the group consisting of dermal, cardiac, cartilage, bone, urothelial, endocrine, neuronal, pancreatic, renal, hepatic and ocular tissue types.

* * * * *